United States Patent
Galliher et al.

(10) Patent No.: US 9,109,193 B2
(45) Date of Patent: *Aug. 18, 2015

(54) CONTINUOUS PERFUSION BIOREACTOR SYSTEM

(75) Inventors: Parrish M. Galliher, Littleton, MA (US); Geoffrey L. Hodge, Sutton, MA (US); Michael Fisher, Ashland, MA (US); Patrick Guertin, Mendon, MA (US); Dan Mardirosian, Charlton, MA (US)

(73) Assignee: GE Healthcare Bio-Sciences Corp., Piscataway, NJ (US)

( * ) Notice: Subject to any disclaimer, the term of this patent is extended or adjusted under 35 U.S.C. 154(b) by 497 days.

This patent is subject to a terminal disclaimer.

(21) Appl. No.: 12/124,039

(22) Filed: May 20, 2008

(65) Prior Publication Data

US 2009/0035856 A1    Feb. 5, 2009

Related U.S. Application Data

(60) Provisional application No. 60/962,671, filed on Jul. 30, 2007.

(51) Int. Cl.
*C12N 5/02* (2006.01)
*C12M 1/00* (2006.01)
(Continued)

(52) U.S. Cl.
CPC ............ *C12M 29/10* (2013.01); *C12M 23/14* (2013.01); *C12M 23/48* (2013.01); *C12M 27/02* (2013.01); *C12M 27/20* (2013.01)

(58) Field of Classification Search
CPC ...... C12M 23/14; C12M 23/48; C12M 27/02; C12M 27/201; C12M 29/10
USPC ............ 435/294.1, 383; 366/102; 200/495.06
See application file for complete search history.

(56) References Cited

U.S. PATENT DOCUMENTS

| 4,727,040 A | 2/1988 | Freedman et al. |
| 6,432,698 B1 | 8/2002 | Gaugler et al. |

(Continued)

FOREIGN PATENT DOCUMENTS

| CA | WO 00/68357 A1 | 11/2000 | ............... C12M 1/16 |
| DE | 20 2007 005884 U1 | 7/2007 | ............... C12M 1/24 |

(Continued)

OTHER PUBLICATIONS

European Search Report, dated Sep. 7, 2011, for Application No. 08161344.0-1521/2020433, 10 pages (in English) (Family Member).

(Continued)

*Primary Examiner* — Michael Hobbs
(74) *Attorney, Agent, or Firm* — Ziegler IP Law Group, LLC.

(57) ABSTRACT

Systems and methods for containing and manipulating liquids, including vessels and unit operations or components of cell culture, cell containment, bioreactor, and/or pharmaceutical manufacturing systems, are provided. In certain embodiments, such vessels and unit operations are directed to continuous perfusion reactor or bioreactor systems and may include one or more disposable components. For instance, in one aspect, a system includes an apparatus in the form of a bioreactor for harvesting cells which produce one or more products. The apparatus may include a disposable, collapsible bag adapted for containing a liquid, the collapsible bag in fluid communication with a liquid-solids (e.g., cell) separation device. For example, an outlet of the collapsible bag may be connected to an inlet of the separation device, and an outlet of the separation device may be connected to an inlet of the collapsible bag for recycle. Accordingly, after separating the cells from the liquid in the separation device, the cells can be flowed back into the collapsible bag where they can be reharvested. Meanwhile, product contained in the liquid can be collected in a separate container. The efficiency of product formation in such a system may be enhanced by using mixing systems described herein.

20 Claims, 11 Drawing Sheets

(51) Int. Cl.
*C12M 3/00* (2006.01)
*C12M 1/06* (2006.01)

(56) References Cited

U.S. PATENT DOCUMENTS

| | | | |
|---|---|---|---|
| 6,544,424 | B1 | 4/2003 | Shevitz |
| 6,544,788 | B2 | 4/2003 | Singh |
| 6,596,521 | B1 * | 7/2003 | Chang et al. ............... 435/136 |
| 2001/0034058 | A1 | 10/2001 | Kopf |
| 2002/0168766 | A1 | 11/2002 | Gold et al. |
| 2003/0119185 | A1 * | 6/2003 | Berenson et al. ............ 435/372 |
| 2005/0226794 | A1 | 10/2005 | Hodge et al. |
| 2005/0272146 | A1 * | 12/2005 | Hodge et al. ............... 435/289.1 |
| 2008/0139865 | A1 * | 6/2008 | Galliher et al. ............. 588/249 |

FOREIGN PATENT DOCUMENTS

| | | | | |
|---|---|---|---|---|
| DE | 202007005884 | | 8/2007 | |
| EP | 0 200 792 | A1 | 11/1986 | ............ C12M 1/02 |
| EP | 0 200 792 | | 5/1990 | |
| EP | 1 065 005 | | 4/2000 | |
| EP | 1 065 005 | A2 | 1/2001 | ............ B05C 11/10 |
| FR | 2 799 138 | | 4/2001 | |
| FR | 2 799 138 | A1 | 4/2001 | ............ B01J 19/24 |
| GB | 2 202 549 | | 9/1988 | |
| GB | 2 202 549 | A | 9/1988 | ............ C12M 1/00 |
| WO | WO 00/68357 | | 11/2000 | |
| WO | WO 03/006633 | | 1/2003 | |
| WO | WO 03/006633 | A1 | 1/2003 | ............ C12N 5/02 |
| WO | WO 2005/076093 | | 8/2005 | |
| WO | WO 2005/108546 | | 11/2005 | |
| WO | WO 2005/118771 | A2 | 12/2005 | |
| WO | WO 2007/050971 | | 5/2007 | |
| WO | WO 2007/109709 | | 9/2007 | |
| WO | WO 2007/109709 | A2 | 9/2007 | ............ G01M 3/04 |
| WO | WO 2008/006494 | | 1/2008 | |
| WO | WO 2008/088379 | | 7/2008 | |
| WO | WO 2008/088379 | A2 | 7/2008 | ............ C12M 1/00 |

OTHER PUBLICATIONS

Communication of a Notice of Opposition Mailed Jan. 8, 2014 on Corresponding EP Application No. 08161344.0.

* cited by examiner

CONTINUOUS PERFUSION BIOREACTOR SYSTEM

RELATED APPLICATIONS

This application claims priority under 35 U.S.C. §119(e) to U.S. Provisional Patent Application No. 60/962,671, filed Jul. 30, 2007, and entitled "Continuous Perfusion Bioreactor System", which is incorporated herein by reference.

FIELD OF INVENTION

The present invention relates in certain aspects to systems and methods for containing and manipulating liquids, and in some embodiments, to vessels and unit operations or components of cell culture, cell containment, bioreactor, and/or pharmaceutical manufacturing systems. In certain embodiments, such systems and methods involve continuous perfusion bioreactors.

BACKGROUND

A variety of vessels, devices, components and unit operations for manipulating liquids and/or for carrying out chemical, biochemical and/or biological processes are available. For instance, biological materials (e.g., animal and plant cells) including, for example, mammalian, plant or insect cells and microbial cultures can be processed using bioreactors. Manufacturing of complex biological products such as proteins (e.g., including monoclonal antibodies, peptides, and hormones) require multiple steps ranging from fermentation or cell culture (bacteria, yeast, insect or fungi), to primary recovery, and finally, to purification. Conventional manufacturing of biotechnology products is generally accomplished using batch or fed-batch processing through a series of unit operations with subsequent off-line laboratory analysis conducted on representative samples collected from various points of the process to ensure quality.

In some cases, increased efficiency may be achieved using continuous bioprocessing compared to batch or fed-batch operations. The increased efficiency can stem from reduced loss of production time to equipment turnaround and smaller, more productive machinery. In operations such as certain bioreactions, fresh cell culture media may be pumped into and out of the bioreactor continuously, maintaining a constant volume of culture in the reactor. Furthermore, cell retention in the bioreactor or cell recycle from the harvest stream out of the bioreactor can be performed such that cells are not lost via product removal from the bioreactor. This maintenance of high cell density in the bioreactor can improve production rates of the bioreaction compared to batch systems.

Although manufacturing systems such as chemical manufacturing systems, pharmaceutical manufacturing systems, and bioreactor systems are known, improvements to such systems would be useful in a variety of fields. In particular, as recognized by the present inventors in the context of the present invention, systems which include disposable components specially configured for performing continuous perfusion would be beneficial.

SUMMARY OF THE INVENTION

The present invention relates in certain aspects to systems and methods for containing and manipulating liquids. The systems and methods may involve, in some embodiments, vessels and unit operations or components of cell culture, cell containment, bioreactor, and/or pharmaceutical manufacturing systems. In certain embodiments, such vessels and unit operations are directed to continuous perfusion mixing, chemical reactor or bioreactor systems. The subject matter of the present invention involves, in some cases, interrelated products, alternative solutions to a particular problem, and/or a plurality of different uses of one or more systems and/or articles.

In one aspect, a series of systems is provided. In one embodiment, a system comprises a first apparatus. The first apparatus comprises a first collapsible bag adapted for containing a liquid, the first collapsible bag including at least one inlet, at least one outlet, and a base plate that is attached to the collapsible bag and configured to support an impeller. The first apparatus also includes a first reusable support structure adapted for surrounding and supporting the first collapsible bag. The system may also include a second apparatus in fluid communication with the first apparatus, the second apparatus including at least one inlet and at least one outlet, wherein an outlet of the first collapsible bag is in fluid communication with an inlet of the second apparatus, and an outlet of the second apparatus is in fluid communication with an inlet of the first collapsible bag.

In another embodiment a system comprises a first apparatus in the form a portable module. The module comprises a first collapsible bag adapted for containing a liquid and a first reusable support structure adapted for surrounding and supporting the collapsible bag. The system may also comprise a second apparatus in the form a portable module, the second apparatus in fluid communication with the first apparatus, wherein the second apparatus comprises a liquid-solids separation device. Upon fluid communication between the first and second apparatuses, each apparatus can be moved relative to the other without breaking the connection. The first collapsible bag may further include a base plate that is attached to the collapsible bag and configured to support an impeller. Optionally, a shaft may be associated with the base plate. In some cases, an impeller may be associated with the base plate. The impeller may be magnetically driven or may be a direct-shaft driven impeller, for example.

In another embodiment, a system comprises a first apparatus comprising a first collapsible bag adapted for containing a liquid, the first collapsible bag including at least one inlet and at least one outlet. The first apparatus also includes a first reusable support structure adapted for surrounding and supporting the first collapsible bag. A second apparatus may be in fluid communication with the first apparatus. The second apparatus may comprise a second collapsible bag adapted for containing a liquid, the second collapsible bag including at least one inlet and at least one outlet. The second apparatus may also include a second reusable support structure adapted for surrounding and supporting the second collapsible bag, wherein an outlet of the first collapsible bag is in fluid communication with an inlet of the second collapsible bag, and an outlet of the second collapsible bag is in fluid communication with an inlet of the first collapsible bag. The first collapsible bag may further include a base plate that is attached to the collapsible bag and configured to support an impeller. Optionally, a shaft may be associated with the base plate. In some cases, an impeller may be associated with the base plate. The impeller may be magnetically driven or may be a direct-shaft driven impeller.

In another embodiment, a system comprises a first apparatus including a first collapsible bag adapted for containing a liquid and a first reusable support structure adapted for surrounding and supporting the collapsible bag. The system also includes a second apparatus in fluid communication with the first apparatus, the second apparatus comprising a centrifuge adapted for separating a plurality of particulates or solid objects from a liquid-solids mixture.

In one aspect, a series of methods are provided. In one embodiment, a method comprises transferring a first liquid comprising a plurality of particulates or solid objects from a first collapsible bag to an apparatus including a liquid-solids separation device. The first collapsible bag may be supported by a first reusable support structure adapted for surrounding and supporting the first collapsible bag. The method also includes separating at least a portion of the plurality of particulates or solid objects from the first liquid in the apparatus, and transferring a second liquid from the apparatus to the first collapsible bag, wherein the first and second liquids have different concentrations of the particulates or solid objects. The apparatus may be external or internal to the collapsible bag.

In another embodiment, a method comprises continuously introducing a first liquid into a collapsible bag comprising an impeller, the first liquid having a first concentration of a particulate or solid object. The collapsible bag may be supported by a reusable support structure adapted for surrounding and supporting the collapsible bag. The method may include continuously removing a second liquid from the collapsible bag, the second liquid having a second concentration of the particulate or solid objects, wherein the first and second concentrations of the particulate or solid objects is different. A substantially constant volume within the collapsible bag may be maintained during the introducing and removing steps. In some embodiments, the second liquid is substantially homogenous with respect to liquid remaining in the collapsible bag immediately after removal, such that the concentration of the particulate or solid objects in the second liquid removed from the collapsible bag is substantially equivalent to the concentration of the particulate or solid objects in the liquid remaining in the collapsible bag immediately after removal.

In another embodiment, a method comprises introducing a first liquid into a collapsible bag comprising an impeller, the first liquid having a first concentration of a particulate or solid objects, wherein the collapsible bag is supported by a reusable support structure adapted for surrounding and supporting the collapsible bag. The method also includes mixing the first liquid in the collapsible bag using the impeller and removing a second liquid from the collapsible bag. The second liquid may have a second concentration of the particulate or solid objects, wherein the first and second concentrations of the particulate or solid object is different. The second liquid may be substantially homogenous with respect to liquid remaining in the collapsible bag immediately after removal, such that the concentration of the particulate or solid objects in the second liquid removed from the collapsible bag is substantially equivalent to the concentration of the particulate or solid objects in the liquid remaining in the collapsible bag immediately after removal. The method also includes causing a liquid to flow from the collapsible bag to an apparatus and causing a liquid to flow from the apparatus to the collapsible bag.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures.

DETAILED DESCRIPTION

Figure 1:
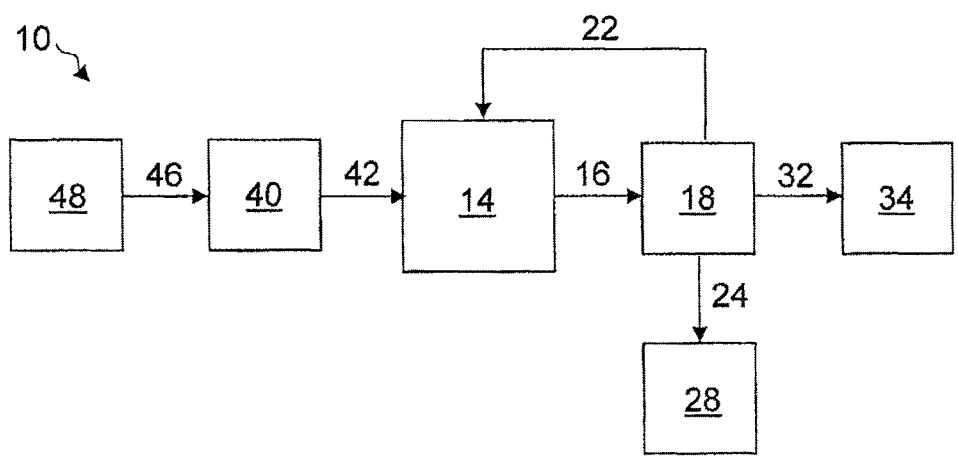
FIG. 1 is a schematic diagram showing fluidic interconnection of several apparatuses, according to an embodiment of the invention.

The present invention relates in certain aspects to systems and methods for containing and manipulating liquids, which may involve, in some embodiments, vessels and unit operations or components of cell culture, cell containment, bioreactor, and/or pharmaceutical manufacturing systems. In certain embodiments, such vessels and unit operations are directed to continuous perfusion mixing, chemical reactor or bioreactor systems and may include one or more disposable components. For instance, in one aspect, a system of the invention includes an apparatus in the form of a bioreactor for growing and, optionally, harvesting cells which produce one or more products. The apparatus may include a disposable, collapsible bag adapted for containing a liquid, the collapsible bag being in fluid communication with a liquid-solids (e.g., cell) separation device. For example, an outlet of the collapsible bag may be connected to an inlet of the separation device, and an outlet of the separation device may be connected to an inlet of the collapsible bag to facilitate recycle of separated solids, e.g. cells, to a reactor/bioreactor of the invention. Accordingly, in certain embodiments, after separating cells from the liquid in the separation device, some or all of cells can be flowed back into the collapsible bag. Meanwhile, product contained in the liquid can be collected in a separate container. The efficiency of product formation in such a system may be enhanced by using mixing systems described herein.

Advantageously, the separation device and/or other devices associated with the reactoribioreactor may also include one or more disposable components such as collapsible bags. Single-use fluid manipulation systems can simplify the complexity and cost of performing continuous perfusion by eliminating the need for cleaning and steam sterilization. Hence, piping complexity may be reduced and the system can be set up quickly and inexpensively compared to certain non-disposable, stainless steel systems.

The following documents are incorporated herein by reference in their entirety: International Patent Application Serial No. PCT/US2008/001051, filed Jan. 25, 2008 and entitled, "Information Acquisition and Management Systems and Methods in Bioreactor Systems and Manufacturing Facilities" by Galliher et al.; U.S. patent application Ser. No. 12/011,492, filed Jan. 25, 2008 and entitled, "Information Acquisition and Management Systems and Methods in Bioreactor Systems and Manufacturing Facilities" by Galliher et al.; International Patent Application Serial No. PCT/US2008/001005, filed Jan. 25, 2008 entitled "Bag Wrinkle Remover, Leak Detection Systems, and Electromagnetic Agitation for Liquid Containment Systems" by Galliher et al.; U.S. application Ser. No. 12/011,493, filed Jan. 25, 2008 entitled "Bag Wrinkle Remover, Leak Detection Systems, and Electromagnetic Agitation for Liquid Containment Systems" by Galliher et al.; U.S. Provisional Application Ser. No. 61/039,382, filed Mar. 25, 2008, entitled "Temperature Control System"; U.S. patent application Ser. No. 12/039,052, filed Feb. 28, 2008, entitled "Weight Measurements of Liquids in Flexible Containers," by P. A. Mitchell, et al.; U.S. patent application Ser. No. 11/879,033, filed Jul. 13, 2007, entitled "Environmental Containment Systems," by G. Hodge, et al.; International Patent Application Serial No. PCT/US2007/015954, filed Jul. 13, 2007 entitled, "Environmental Containment Systems" by Galliher et al.; International Patent Application Serial No. PCT/US2007/014050 filed on Jun. 15, 2007 and entitled, "Gas Delivery Configurations, Foam Control Systems, and Bag Molding Methods and Articles for Collapsible Bag Vessels" by Fisher et al.; U.S. patent application Ser. No. 11/818,901 filed on Jun. 15, 2007 and entitled, "Gas Delivery Configurations, Foam Control Systems, and Bag Molding Methods and Articles for Collapsible Bag Vessels" by Fisher et al.; U.S. patent application Ser. No. 11/147,124, filed Jun. 6, 2005, entitled "Disposable Bioreactor Systems and Methods," by G. Hodge, et al., published as U.S. Patent Application Publication No. 2005/0272146 on Dec. 8, 2005; International Patent Application No. PCT/US2005/020083, filed Jun. 6, 2005, entitled "Disposable Bioreactor Systems and Methods," by G. Hodge, et al., published as WO 2005/118771 on Dec. 15, 2005; U.S. patent application Ser. No. 11/050,133, filed Feb. 3, 2005, entitled "System and Method for Manufacturing," by G. Hodge, et al., published as U.S. Patent Application Publication No. 2005/0226794 on Oct. 13, 2005; and International Patent Application No. PCT/US2005/002985, filed Feb. 3, 2005, entitled "System and Method for Manufacturing," by G. Hodge, et al., published as WO 2005/076093 on Aug. 18, 2005.

Although much of the description herein involves an exemplary application of the present invention related to bioreactors (and/or biochemical and chemical reaction systems including liquid-containing vessels), the invention and its uses are not so limited, and it should be understood that aspects of the invention can also be used in other settings, including those involving containment systems in general, systems for containment and/or processing of a fluid (e.g., a liquid or a gas) in a container (e.g., mixing systems and filtration systems), as well as systems related to a biological, chemical, and/or pharmaceutical manufacturing process (e.g., primary recovery, filtration and chromatography systems, cell culture systems, microscopy and/or other analytical devices, etc.). It should also be understood that while many examples provided herein involve the use of vessels comprising collapsible bags or flexible containers, aspects of the invention can be integrated with vessels comprising non-collapsible or rigid containers, and other configurations involving liquid containment.

In one aspect of the invention, a system for containing and manipulating fluids is provided. As shown in the process illustrated in FIG. 1, system 10 includes an apparatus 14 which can comprise a vessel. In general, for simplicity and conciseness, unless prohibited by the surrounding context, the term "vessel" may be used as a shorthand for indicating a volumetric container adapted for containing a liquid, or a support structure for supporting a volumetric container, or a unit operation component, or another device or component thereof forming at least part of a cell culture, cell containment, bioreactor, chemical manufacturing, pharmaceutical manufacturing, or other manufacturing system. Non-limiting examples of unit operation components include stirred-tank bioreactors, filtration systems, seed culture expansion systems, primary recovery systems, chromatography systems, filling systems, closed media/buffer preparation systems, and water purification systems (e.g., water for injection (WFI) systems). The shorthand term "vessel" may be used to apply to any of these and others.

In some embodiments, apparatus 14 includes one or more disposable components. For example, as described in more detail below, apparatus 14 may comprise a reactor for forming a chemical, biological, and/or pharmaceutical product in the form of a disposable, collapsible bag adapted for containing a liquid. The collapsible bag may be supported by and may line an inner surface of a reusable support structure.

In certain embodiments, apparatus 14 contains a liquid comprising viable and/or non-viable components such as particulates and solid objects (e.g., cells, beads, precipitates, crystals, etc.). As used herein, a "solid object" when used in the context of a material contained in or carried by a liquid, is an object that does not dissolve in or otherwise form a miscible solution with the liquid. Solid objects are not necessarily completely solid, and may include, in some embodiments, individual entities that may be deformable, such as cells, organisms, and gelatinous particles. The solid objects may or may not form a stable suspension (e.g., a colloidal suspension), depending on the size and buoyancy of the solid objects and the surface properties of the solid objects and the thermodynamic properties of the liquid. In some embodiments, components including particulates and solid objects may be used as part of a biological, chemical, and/or pharmaceutical manufacturing process to generate one or more products or may comprise a product themselves. For example, apparatus 14 may be used to produce a variety of products from various solid objects such as, e.g., bacteria, insect cells, fungi, mammalian cells, human cells, organs, yeast, protozoa, nematodes, viruses, algae, and plant cells. Higher organisms such as insects, plants, fish, and shrimp can also comprise the solid objects and be used to generate one or more products. Additional examples of such solid objects are described in more detail below. Non-viable solid objects that may be contained in an apparatus include, for example, beads (e.g., cytodex beads), precipitates, and crystals of biological or non-biological nature.

Apparatus 14 can be configured to be in fluid communication with apparatus 18, which may also include a vessel adapted for containing a liquid. Fluid communication may be continuous in some embodiments, or periodic in other embodiments. In some cases, a liquid can be transferred 16 from apparatus 14 to apparatus 18, where a manipulation of the liquid can take place. Manipulation may include, for example, mixing, aeration, separation, filtration, causing a reaction to occur, changing a concentration of a component in the liquid, and the like. In some cases, manipulation of the liquid takes place during transfer. For example, a tube connecting the apparatuses may include a filter for separating solid objects from the liquid. In other cases, manipulation of the liquid takes place while the liquid is contained in apparatus 18. For instance, apparatus 18 may comprise a separation device (e.g., a centrifuge, a hollow fiber column, or other suitable device) for separating a component from the liquid. In some cases, the separation device is a liquid-solids separation device that separates particulates or solid objects from the liquid.

Like apparatus 14, apparatus 18 may, in some embodiments, include one or more disposable components such as a collapsible bag adapted for containing a liquid. The collapsible bag may be supported by and may line an inner surface of a reusable support structure. For example, in one particular embodiment, apparatus 18 is in the form of a centrifuge that includes a disposable, collapsible bag that contains the liquid to be manipulated.

Advantageously, for certain embodiments including disposable components and reusable support structures, because the liquid in the collapsible bag does not come into contact with the support structure, the support structure can be reused without cleaning. That is, after a fluid manipulation or other process takes place in the collapsible bag, the container can be removed from the support structure and replaced by a second (e.g., disposable) container. A second fluid manipulation or process can be carried out in the second container without having to clean either the first container or the reusable support structure.

In other embodiments, disposable components other than disposable containers can be associated with an apparatus. For instance, disposable filtration elements, sensors, sampling devices, pumps, valves, and mixers can be used in combination with apparatuses described herein.

In some embodiments, an outlet of apparatus 14 is in fluid communication with an inlet of apparatus 18, and an outlet of apparatus 18 is in fluid communication with an inlet of apparatus 14. Thus, a first liquid may flow from apparatus 14 to apparatus 18 and a second liquid may flow from apparatus 14 to apparatus 18, where the first and second fluids may be the same or different. In such embodiments, recycling of a liquid occurs between apparatuses 14 and 18. For example, after a manipulation of a first liquid takes place in apparatus 18, a second liquid can be transferred 22 to apparatus 14. In some cases, the second liquid has a different composition and/or concentration of a component (e.g., a particulate or solid object) than that of the first liquid.

In one embodiment, apparatus 18 is a cell separation device (e.g., a centrifuge or filter) that separates cells from a first liquid contained in apparatus 14. After separation, the cells may be delivered back to apparatus 14 in the form of a second liquid suspension (e.g., a retentate) for continued growth/harvesting. Meanwhile, the remaining liquid that was separated (e.g., the permeate, a third liquid) can be transferred 24 and collected in apparatus 28. In some instances, the third liquid includes a product produced by the cells. The product may be isolated (e.g., purified) and/or processed further using apparatus 28. For instance, apparatus 28 can include a vessel such as a disposable, collapsible bag for retaining the liquid, e.g., a storage bag, or for containing the liquid for further manipulation.

Additionally or alternatively, all or a portion of a liquid from apparatus 18 can be transferred 32 to apparatus 34, where the liquid can be processed further. For example, where the third liquid contains a product, the product can be used as a reactant in a chemical, biological, and/or pharmaceutical reaction that takes place in apparatus 34. Accordingly, like apparatuses 14 and 18, apparatus 34 can include one or more unit operation components such as a reactor for performing a biological, chemical, and/or pharmaceutical manufacturing process or step thereof.

Optionally, in some embodiments apparatus 14 is in fluid communication with one or more apparatuses 40. For instance, liquid may be transferred 42 continuously or periodically from apparatus 40 to apparatus 14. Apparatus 40 may include, for example, a vessel such as a storage tank adapted for containing media, buffer, reactants, and/or other fluids. A plurality of apparatuses 40 may each contain different media, buffer, reactants, and/or other liquids to be transferred to apparatus 14. One or more apparatuses 40 may include disposable components such as a collapsible bag adapted for containing a liquid, the collapsible bag optionally being supported and contained by a reusable support structure.

In some cases, transfer 42 occurs while transfer 16 takes place between apparatuses 14 and 18. In some such embodiments, continuous perfusion reactions or bioreactions can be performed. For example, in one particular embodiment, as a first liquid containing a relatively low concentration of cells is being transferred from apparatus 14 to apparatus 18, separation of the cells and the liquid can take place in apparatus 18. A second liquid (e.g., a retentate) containing a relatively high concentration of cells can be transferred 22 back to apparatus 14 to perform cell recycling. Meanwhile, media or other reagents can be transferred from apparatus 40 to apparatus 14. In certain such embodiments, apparatus 18 is configured to receive a first liquid comprising a first concentration of a component (e.g., cells) from apparatus 14 and to deliver a second liquid comprising a second concentration of the component. As mentioned, the first and second concentrations can be the same in some cases, and different in other cases.

In some cases, transfer 42 and transfer 16 take place simultaneously such that a substantially constant volume is maintained in apparatus 14. As used herein, a "substantially constant volume" process refers to a process in which a reaction or other liquid manipulation process takes place in an apparatus containing a volume of liquid whose volume does not change by more than 10% in certain embodiment, or in other embodiments does not change by more than 5%, by more than 1%, by more than 0.5%, or by more than 0.1% throughout the course of the process. In the case of an apparatus including a vessel (e.g., a reactor), the vessel is said to operate at a substantially constant volume when the above mentioned conditions are satisfied.

Measurement of volume, including a substantially constant volume, in an apparatus may be performed by a variety of methods including, but not limited to, the use of one or more load cells positioned underneath supports or legs of the apparatus, as well as methods described in U.S. patent application Ser. No. 12/039,052, filed Feb. 28, 2008, entitled "Weight Measurements of Liquids in Flexible Containers," by P. A. Mitchell, et al., which is incorporated herein by reference.

Advantageously, in some embodiments, apparatus 14 is designed to generate a liquid that is substantially homogeneously mixed. A liquid is "substantially homogenously mixed" when a first portion of the liquid at a first location within the apparatus contains substantially the same concentration of components (e.g., particulates, solid objects, gases, nutrients, etc.) as a second portion of the liquid at a second location within the apparatus, wherein the first and second locations are physically separated by a distance equal to at least one half a distance defining a maximum cross-sectional dimension of the wetted portion of the apparatus containing the liquid. "Substantially the same concentration" as used in the above context refers to the concentration at the first location differing from the concentration at the second location by no more than 10% in certain embodiments, and in other embodiments, by no more than 5%, by no more than 1%, by no more than 0.5%, or by no more than 0.1%. The first and second locations may be, for example, top and bottom portions of the apparatus. In some such embodiments, apparatus 14 includes a mixer, e.g., in the form of a magnetically-driven impeller, that has a high efficiency of mixing within the apparatus. For instance, in some cases, the mixing time, which may be defined by how long it takes to reach substantial homogeneity after an addition, may be less than 10% of the average residence time of a fluid element in the apparatus. In other cases, the residence time is less than 8%, less than 6%, less than 4%, or less than 2% of the average residence time of a fluid element in the apparatus. Examples of magnetically-driven impellers, which may be disposable and adapted for single use in some cases, are described in more detail below.

An apparatus including a mixer described herein may allow removal of essentially homogenous portions of a liquid from the apparatus. For example, a liquid portion removed from the apparatus may be essentially homogenous with respect to liquid remaining in the apparatus immediately after removal, such that the concentration of a component (e.g., a particulate, solid object, gas, nutrient, etc.) in the liquid portion removed from the apparatus is substantially equivalent to the concentration of the component in the liquid remaining in the apparatus immediately after removal (i.e., differing in concentration by an amount within the limits as defined with respect to "substantially homogeneously mixed" above). When combining substantially homogeneously mixed liquids with a liquid recycling system (e.g., a system where an outlet of a first apparatus is connected to an inlet of a second apparatus, and an outlet of the second apparatus is connected to an inlet of the first apparatus), and optionally with apparatuses including one or more disposable components (e.g., collapsible bags), systems of the invention may have increased efficiency in forming a biological, chemical, and/or pharmaceutical products compared to known systems. For instance, when systems of the invention are used to culture cells or higher organisms to form a product, well-mixed liquids in an apparatus can increase the viability of the cells or organisms, as nutrients required by the cells or organisms are well dispersed within the liquid. Thus, the number and size of unmixed zones, which may be lead to perturbations and less efficient product formation, may decrease.

Referring again to FIG. 1, system 10 may optionally include one or more apparatuses 48 in fluid communication with apparatus 40. Apparatus 48 may comprise, for example, a mixing system that generates the solutions to be stored in one or more apparatuses 40. Apparatus 48 may include, in some embodiments, a magnetically-driven impeller and/or a collapsible bag, which may be optionally integrated together as a single unit and designed to be disposable.

In some embodiments, each of the apparatuses associated with a system described herein (e.g., system 10 of FIG. 1) includes one or more disposable components. In certain such embodiments, each of the apparatuses includes a disposable, collapsible bag (e.g., liner).

As mentioned above, fluid communication between each of the apparatuses may be continuous or periodic. Periodic fluid communication between two apparatuses may be controlled by one or more components such as intermediate control valves, check valves, pumps, or the like. Restricted fluid communication between apparatuses can also take place. For instance, a filter or other device may enable liquid but not a substantial quantity of particulates solid objects and/or undesirable agents to pass from one apparatus to another. In addition, one or more pressure gauges, sensors, pumps, and/or other components can be positioned between apparatuses for monitoring flow, transferring fluid, or for other purposes.

It should be understood that not all of the apparatuses shown in FIG. 1 need be present in all embodiments of the invention and that the illustrated apparatuses may be otherwise positioned or configured and certain embodiments may employ additional apparatuses beyond those illustrated. For example, additional apparatuses including other unit operation components or elements may be present in other embodiments, as described in more detail below.

Optionally, apparatuses described herein may include an environmental containment enclosure. An "environmental containment enclosure" as used herein refers to an enclosure at least partially surrounding and creating a substantially closed or closable space (an "enclosed space") having, when in operation, a sterile, aseptic, substantially particle-free, or reduced-particle environment inside the enclosure (as compared to an environment surrounding the enclosure). The containment apparatus may be in fluid communication with a ventilation system that helps to maintain such an environment inside the containment apparatus. The ventilation system may be external to the enclosure or could be partially or completely contained within the enclosure. Alternatively, instead of or in addition to a ventilation system, some other environmental treatment system may be used to create and maintain a sterile, aseptic, substantially particle-free, or reduced-particle environment, such as, for example, an ultraviolet and/or other form of radiation sterilizer, a source of steam, ethylene oxide and/or other disinfectant, etc. In addition to the description herein, environmental containment enclosures, components, and methods associated therewith are described in more detail in an International Patent Application and a U.S. patent application filed Jul. 13, 2007 entitled, "Environmental Containment Systems" by Galliher et al., each of which is incorporated herein by reference.

In certain embodiments, especially embodiments involving large vessels, the environmental containment enclosure has a shape and/or contour that is complementary to a shape and/or contour of a vessel to which the enclosure is attached to allow access to a material contained in the vessel from various locations around the vessel. The complementary shape and/or contour also reduces the overall size and/or footprint of the vessel and containment enclosure combination. In certain embodiments, access is achieved without subjecting the material to an external atmosphere surrounding the environmental containment enclosure(s). Accordingly, such environmental containment can prevent or decrease the amount of contamination, e.g., from personnel, equipment, and ambient air, of a material contained in the vessel or the degree of exposure of a user to the material. These systems may be particularly useful for producing and/or isolating toxins or other infectious materials within the vessel with improved safety.

By including environmental containment for apparatuses described herein, integrity and control of the environment inside the apparatus can be achieved for one or more steps of a manufacturing process. Accordingly, in some embodiments, apparatuses may be used in an unclassified ambient space, thereby saving costs associated with otherwise forming and/or maintaining a clean room facility. Additionally, environmental conditions within the apparatuses may be classified in a manner consistent with normal process suite classifications for typical manufacturing systems. For example, an apparatus used for bioreactor fermentation may be operated as unclassified, while apparatuses designed for purification may be classified as Class 10,000. Seed and bulk drug substance fill apparatus environments may be classified as Class 100 environments. Those of ordinary skill in the art can determine the appropriate environments required for performing particular biological, chemical, and/or pharmaceutical manufacturing processes. Furthermore, in some embodiments, an environmental treatment system comprising an in-situ decontamination system may be associated with an apparatus for cleaning an interior of the apparatus and/or for maintaining a sterile, aseptic, substantially particle-free, or reduced-particle environment within the apparatus.

Figure 2:
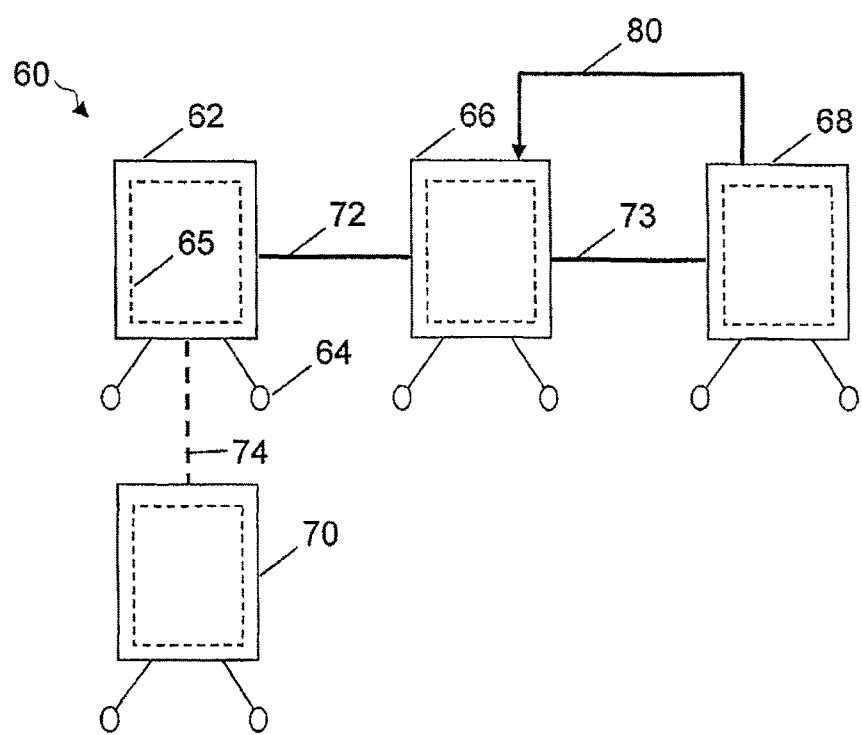
FIG. 2 is a schematic diagram showing fluidic interconnection of several individually portable apparatuses, according to an embodiment of the invention.

In some embodiments, apparatuses of the invention are configured as individual mobile modules that can be interconnected with other modules. The modules may be used, in some embodiments, to perform a series of steps relating to a biological, chemical, and/or pharmaceutical (e.g., biopharmaceutical) manufacturing process or other fluid manipulation process. For instance, as shown in the embodiment illustrated in FIG. 2, system 60 includes a first apparatus 62 having wheels 64 or other components for facilitating movement and/or portability of the apparatus. Optionally, the first apparatus can be connected to second apparatus 66 via connection 72.

Connection between apparatuses may take place through a variety of means such as, for example, a rigid or flexible tube, a latch, or the like. In some instances, a flexible connection between the apparatuses is formed, allowing each of the apparatuses to be moved in different orientations with respect to one another even when interconnected. For example, upon fluid communication between apparatuses, each apparatus can be moved relative to the other without breaking the connection. This feature can facilitate transport of the apparatuses, especially around tight corners. Interconnection between apparatuses and methods associated therewith are described in more detail in U.S. patent application Ser. No. 11/050,133, filed Feb. 3, 2005, entitled "System and Method for Manufacturing," by G. Hodge, et al., published as U.S. Patent Application Publication No. 2005/0226794 on Oct. 13, 2005; International Patent Application No. PCT/US2005/002985, filed Feb. 3, 2005, entitled "System and Method for Manufacturing," by G. Hodge, et al., published as WO 2005/076093 on Aug. 18, 2005; and International Patent Application and U.S. patent application filed Jul. 13, 2007 entitled, "Environmental Containment Systems" by Galliher et al., each of which is incorporated herein by reference.

Connection between apparatuses 62 and 66 can be formed before, during, and/or after a process has been performed in first apparatus 62. In some embodiments, connection 72 allows fluid communication between the apparatuses. This arrangement can allow, in some cases, a material within an interior of apparatus 62 to be transferred to an interior portion of apparatus 66. In apparatuses including an environmental containment enclosure, connection may involve fluid communication between the enclosures. Fluid communication between the enclosures may occur independently, or together with fluid communication between the interiors of the apparatuses. Optionally, the apparatuses can be connected physically but without fluid communication between interiors of the apparatuses.

Transfer of a material from apparatus 62 to apparatus 66 can allow the material to be further processed or manipulated in apparatus 66, which may have a different functionality than that of apparatus 62 (e.g., a different unit operation component). For instance, while apparatus 62 may include a vessel in the form of a reactor for producing a biological, chemical and/or pharmaceutical material, apparatus 66 may include a vessel configured to purify the material formed in apparatus 62.

If further processing or manipulation of the material within apparatus 66 is required, apparatus 66 can be interconnected with apparatus 68 via connection 73 in a manner described above in connection with apparatuses 62 and 66. Apparatus 68 may be designed and configured to perform a different process than that of apparatus 66; for instance, apparatus 66 may include a vessel comprising an ultra filtration system, such as a tangential flow ultra filtration apparatus. Of course, additional apparatuses can be interconnected for performing further processing functions.

In certain embodiments, one or more apparatuses 62, 66, 68, and/or 70 can be associated with its own ventilation system, cooling system, feedback control system, and/or other component or system that can allow the apparatus(es) to be operated independently of one another, if desired.

Advantageously, apparatuses that are configured to be individually mobile/portable can be reconfigured after use to perform a second biological, chemical, or pharmaceutical process or other fluid manipulation process within the apparatus. For instance, after a material within apparatus 62 has been transferred to apparatus 66, apparatuses 62 and 66 can be disconnected and apparatus 62 can be used to perform a second process. In some cases, the second process is unrelated to the first process; for example, the first process may be forming a drug and the second process may be harvesting cells. In other cases, the second process is related to the first process; e.g., the first process may be forming a drug precursor and the second process may be reacting the drug precursor with a compound to form a drug.

The use of disposable components within the apparatuses may facilitate reconfiguration of the apparatuses. For example, in one particular embodiment, apparatus 62 includes a vessel 65, which may be in the form of a disposable, collapsible bag that can be used as a biological, chemical, or pharmaceutical reaction vessel. After a first process has been performed in the disposable bag, and the material has been transferred from apparatus 62 to apparatus 66, the disposable bag can be removed from apparatus 62 and a new disposable bag can be inserted therein. This arrangement can allow a second process to be performed within apparatus 62 while the transferred material is processed in apparatus 66. Likewise, after the second process within apparatus 62 has been accomplished, the material within the apparatus can be transferred to apparatus 66. Alternatively, apparatus 62 can be interconnected with apparatus 70 via connection 74. Accordingly, one or more processes can be performed simultaneously using system 60, saving the user time and space.

In other embodiments, liquid recycling can be performed between two or more apparatuses that are individually mobile or portable. For example, an outlet of apparatus 66 may be connected to an inlet of apparatus 68 via connection 73 (e.g., a tube or other fluid transfer device) and an outlet of apparatus 68 may be connected to an inlet of apparatus 66 via connection 80. In some cases, a first liquid having a first concentration of a component flows from apparatus 66 to apparatus 68, and a second liquid having a second concentration of the component flows from apparatus 68 to apparatus 66. The first and second concentrations may be the same in some embodiments, and different in other embodiments. Optionally, an outlet of apparatus 62 may be connected to an inlet of apparatus 66. In some such systems, a liquid can be continuously introduced into apparatus 66 from apparatus 62 and a liquid can be continuously removed from apparatus 66 to apparatus 68. In some cases, transfer of liquids may be performed such that a substantially constant volume is maintained in apparatus 66. Non-constant volume processes may also be performed. Optionally, a liquid portion removed from apparatus 66 may be substantially homogenous with respect to liquid remaining in apparatus 66 immediately after removal, such that the concentration of a component (e.g., a particulate, solid object, gas, nutrient, etc.) in the liquid portion removed from the apparatus is substantially equivalent to the concentration of the component in the liquid remaining in the apparatus immediately after removal.

Individually mobile apparatuses may be self-sufficient and independently customized to perform a specific biological, chemical, or pharmaceutical process. This can allow, for example, system 60 to be customized to perform a particular process at a first location, disassembled, and then shipped to a second location to perform the same process at the second location. Because each apparatus may be mobile and independently operated, time and expertise required to assemble the apparatuses at the second location may be minimal. Automation of the apparatuses can also facilitate setup and use of the apparatuses at the second location, especially when users at the second location are untrained or unfamiliar with the system. Furthermore, if desired, the use of apparatuses having an environmental containment enclosure can allow the apparatuses to be used in non-sterile or non-clean room environments for processes requiring such environments, since the enclosed space(s) formed by the environmental containment enclosure(s) can be operated under sterile, aseptic, particle-free, or reduced-particle conditions. This feature can substantially save costs as clean room or other facilities may not be required.

As described herein, a variety of components in the form of solid objects or entities dissolved, suspended or otherwise contained in a liquid can be contained in systems and apparatuses of the invention. The solid objects or entities may be used, in some cases, to generate or facilitate generation of one or more products. Non-limiting examples of solid objects include microcarriers (e.g., polymer spheres, solid spheres, gelatinous particles, microbeads, and microdisks that can be porous or non-porous), cross-linked beads (e.g., dextran) charged with specific chemical groups (e.g., tertiary amine groups), 2D microcarriers including cells trapped in nonporous polymer fibers, 3D carriers (e.g., carrier fibers, hollow fibers, multicartridge reactors, and semi-permeable membranes that can comprising porous fibers), microcarriers having reduced ion exchange capacity, cells, capillaries, and aggregates (e.g., aggregates of cells).

In some cases, components contained in a liquid are viable and can include cells or other entities. Non-limiting examples of viable components include cell cultures derived from sources such as animals (e.g., hamsters, mice, pigs, rabbits, dogs, fish, shrimp, nematodes, and humans), insects (e.g., moths and butterflies), plants (e.g., algae, corn, tomato, rice, wheat, barley, alfalfa, sugarcane, soybean, potato, lettuce, lupine, tobacco, rapeseed (canola), sunflower, turnip, beet cane molasses, seeds, safflower, and peanuts), bacteria, fungi, and yeast. In some cases, whole organisms (e.g., insects, crustaceans, etc.) such as ones above can be contained in apparatuses described herein.

Non-limiting examples of animal cells include Chinese hamster ovary (CHO), mouse Myeloma, MO035 (NS0 cell line), hybridomas (e.g., B-lymphocyte cells fused with myeloma tumor cells), baby hamster kidney (BHK), monkey COS, African green monkey kidney epithelial (VERO), mouse embryo fibroblasts (NIH-3T3), mouse connective tissue fibroblasts (L929), bovine aorta endothelial (BAE-1), mouse myeloma lymphoblastoid-like (NS0), mouse B-cell lymphoma lymphoblastoid (WEHI 231), mouse lymphoma lymphoblastoid (YAC 1), mouse fibroblast (LS), hepatic mouse (e.g., MC/9, NCTC clone 1469), and hepatic rat cells (e.g., ARL-6, BRL3A, H4S, Phi 1 (from Fu5 cells)).

Cells from humans can include cells such as retinal cells (PER-C6), embryonic kidney cells (HEK-293), lung fibroblasts (MRC-5), cervix epithelial cells (HELA), diploid fibroblasts (WI38), kidney epithelial cells (HEK 293), liver epithelial cells (HEPG2), lymphoma lymphoblastoid cells (Namalwa), leukemia lymphoblastoid-like cells (HL60), myeloma lymphoblastoid cells (U 266B1), neuroblastoma neuroblasts (SH-SY5Y), diploid cell strain cells (e.g., propagation of poliomyelitis virus), pancreatic islet cells, embryonic stem cells (hES), human mesenchymal stem cells (MSCs, which can be differentiated to osteogenic, chondrogenic, tenogenic, myogenic, adipogenic, and marrow stromal lineages, for example), human neural stem cells (NSC), human histiocytic lymphoma lymphoblastoid cells (U937), and human hepatic cells such as WRL68 (from embryo cells), PLC/PRF/5 (i.e., containing hepatitis B sequences), Hep3B (i.e., producing plasma proteins: fibrinogen, alpha-fetoprotein, transferrin, albumin, complement C3 and/or alpha-2-macroglobulin), and HepG2 (i.e., producing plasma proteins: prothrombin, antithrombin III, alpha-fetoprotein, complement C3, and/or fibrinogen).

In some instances, cells from insects (e.g., baculovirus and *Spodoptera frugiperda* ovary (Sf21 cells produce Sf9 line)) and cells from plants and/or food can be cultured. For instance, cells from sources such as rice (e.g., *Oryza sativa, Oryza sativa* cv Bengal callus culture, and *Oryza sativa* cv Taipei 309), soybean (e.g., *Glycine max* cv Williams 82), tomato (*Lycopersicum esculentum* cv Seokwang), and tobacco leaves (e.g., *Agrobacterium tumefaciens* including Bright Yellow 2 (BY-2), *Nicotiana tabacum* cv NT-1, *N. tabacum* cv BY-2, and *N. tabacum* cv Petite Havana SR-1) can be cultured in various types of apparatuses as described herein.

In other instances, cells from various sources of bacteria, fungi, or yeast can be cultured in apparatuses. Non-limiting examples of bacteria include *Salmonella, Escherichia coli, Vibrio cholerae, Bacillus subtilis, Streptomyces, Pseudomonas fluorescens, Pseudomonas putida, Pseudomonas* sp, *Rhodococcus* sp, *Streptomyces* sp, and *Alcaligenes* sp. Fungal cells can be cultured from species such as *Aspergillus niger* and *Trichoderma reesei*, and yeast cells can include cells from *Hansenula polymorpha, Pichia pastoris, Saccharomyces cerevisiae, S. cerevisiae* crossed with *S. bayanus, S. cerevisiae* crossed with LAC4 and LAC12 genes from *K. lactis, S. cerevisiae* crossed with *Aspergillus shirousamii, Bacillus subtilis, Saccharomyces diastasicus, Schwanniomyces occidentalis, S. cerevisiae* with genes from *Pichia stipitis*, and *Schizosaccharomyces pombe.*

A variety of different end products can be produced in apparatuses described herein. Products can include proteins (e.g., antibodies and enzymes), vaccines, viral products, hormones, immunoregulators, metabolites, fatty acids, vitamins, drugs, antibiotics, cells, and tissues. Non-limiting examples of proteins include human tissue plasminogen activators (tPA), blood coagulation factors, growth factors (e.g., cytokines, including interferons and chemokines), adhesion molecules, Bcl-2 family of proteins, polyhedrin proteins, human serum albumin, scFv antibody fragment, human erythropoietin, mouse monoclonal heavy chain γ, mouse $IgG_{2b/\kappa}$, mouse $IgG_1$, heavy chain mAb, Bryondin 1, human interleukin-2, human interleukin-4, ricin, human α1-antitrypisin, biscFv antibody fragment, immunoglobulins, human granulocyte, stimulating factor (hGM-CSF), hepatitis B surface antigen (HBsAg), human lysozyme, IL-12, and mAb against HBsAg. Examples of plasma proteins include fibrinogen, alpha-fetoprotein, transferrin, albumin, complement C3 and alpha-2-macroglobulin, prothrombin, antithrombin III, alpha-fetoprotein, complement C3 and fibrinogen, insulin, hepatitis B surface antigen, urate oxidase, glucagon, granulocyte-macrophage colony stimulating factor, hirudin/desirudin, angiostatin, elastase inhibitor, endostatin, epidermal growth factor analog, insulin-like growth factor-1, kallikrein inhibitor, α-1 antitrypsin, tumor necrosis factor, collagen protein domains (but not whole collagen glycoproteins), proteins without metabolic byproducts, human albumin, bovine albumin, thrombomodulin, transferrin, factor VIII for hemophilia A (i.e., from CHO or BHK cells), factor VIIa (i.e., from BHK), factor IX for hemophilia B (i.e., from CHO), human-secreted alkaline phosphatase, aprotinin, histamine, leukotrienes, IgE receptors, N-acetylglucosaminyltransferase-III, and antihemophilic factor VIII.

Enzymes can be produced from a variety of sources in apparatuses described herein. Non-limiting examples of such enzymes include YepACT-AMY-ACT-X24 hybrid enzyme from yeast, *Aspergillus oryzae* α-amylase, xylanases, urokinase, tissue plasminogen activator (rt-PA), bovine chymosin, glucocerebrosidase (therapeutic enzyme for Gaucher's disease, from CHO), lactase, trypsin, aprotinin, human lactoferrin, lysozyme, and oleosines.

In some instances, vaccines can be produced. Non-limiting examples include vaccines for prostate cancer, human papilloma virus, viral influenza, trivalent hemagglutinin influenza, AIDS, HIV, malaria, anthrax, bacterial meningitis, chicken pox, cholera, diphtheria, *haemophilus influenza* type B, hepatitis A, hepatitis B, pertussis, plague, pneumococcal pneumonia, polio, rabies, human-rabies, tetanus, typhoid fever, yellow fever, veterinary-FMD, New Castle's Disease, foot and mouth disease, DNA, Venezuelan equine encephalitis virus, cancer (colon cancer) vaccines (i.e., prophylactic or therapeutic), MMR (measles, mumps, rubella), yellow fever, *Haemophilus influenzae* (Hib), DTP (diphtheria and tetanus vaccines, with pertussis subunit), vaccines linked to polysaccharides (e.g., Hib, *Neisseria meningococcus*), *Staphylococcus pneumoniae*, nicotine, multiple sclerosis, bovine spongiform encephalopathy (mad cow disease), IgG1 (phosphonate ester), IgM (neuropeptide hapten), SIgA/G (*Streptococcus mutans* adhesin), scFv-bryodin 1 immunotoxin (CD-40), IgG (HSV), LSC(HSV), Norwalk virus, human cytomegalovirus, rotavirus, respiratory syncytial virus F, insulin-dependent autoimmune mellitus diabetes, diarrhea, rhinovirus, herpes simplex virus, and personalized cancer vaccines, e.g., for lymphoma treatment (i.e., in injectable, oral, or edible forms). In some cases, recombinant subunit vaccines can be produced, such as hepatitis B virus envelope protein, rabies virus glycoprotein, *E. coli* heat labile enterotoxin, Norwalk virus capsid protein, diabetes autoantigen, cholera toxin B subunit, cholera toxin B an dA2 subunits, rotavirus enterotoxin and enterotoxigenic *E. coli*, fimbrial antigen fusion, and porcine transmissible gastroenteritis virus glycoprotein S.

It may be desirable, in some cases, to produce viral products in systems of the invention. Non-limiting examples of viral products include sindbis, VSV, oncoma, hepatitis A, channel cat fish virus, RSV, corona virus, FMDV, rabies, polio, reo virus, measles, and mumps.

Hormones are another class of end products that can be produced in apparatuses described herein. Non-limiting examples of hormones include growth hormone (e.g., human growth hormone (hGH) and bovine growth hormone), growth factors, beta and gamma interferon, vascular endothelial growth factor (VEGF), somatostatin, platelet-derived growth factor (PDGF), follicle stimulating hormone (FSH), luteinizing hormone, human chorionic hormone, and erythropoietin.

Immunoregulators can also be produced in apparatuses described herein. Non-limiting examples of immunoregulators include interferons (e.g., beta-interferon (for multiple sclerosis), alpha-interferon, and gamma-interferon) and interleukins (such as IL-2).

Metabolites (e.g., shikonin and paclitaxel) and fatty acids (i.e., including straight-chain (e.g., adipic acid, Azelaic acid, 2-hydroxy acids), branched-chain (e.g., 10-methyl octadecanoic acid and retinoic acid), ring-including fatty acids (e.g., coronaric acid and lipoic acid), and complex fatty acids (e.g., fatty acyl-CoA)) can also be produced.

In certain embodiments, apparatuses described herein form at least a part of a bioreactor system. The bioreactor system may contain or produce one or more of the entities described above. A non-limiting example of a bioreactor system including a container, such as a flexible container, is shown in the schematic diagram of FIG. 3. As shown in the embodiment illustrated in FIG. 3, apparatus 100 includes a vessel 114, which, in the illustrated embodiment, is a reusable support structure (e.g., a stainless steel tank) that surrounds and contains a container 118. Optionally, apparatus 100 can include an environmental containment enclosure 120, which surrounds a portion of vessel 114.

In some embodiments, container 118 is configured as a collapsible bag (e.g., a polymeric bag). Additionally or alternatively, all or portions of the collapsible bag or other container may be formed of a substantially rigid material such as a rigid polymer, metal, and/or glass. In other embodiments, a rigid container is used in this configuration, wherein inner walls of vessel 114 are in direct contact with the liquid, and container 118 is not present. Container 118 may be disposable and may be configured to be easily removable from support structure 114. Accordingly, container 118 may be reversibly attached to the support structure (i.e., able to be separated by hand or with tools without damage to the components). In other embodiments, container 118 may be irreversibly attached to support structure 114. As used herein, the term "irreversibly attached," when referring to two or more objects, means separation of the two or more objects requires causing damage to at least one of the object (or components of the object), for example, by breaking or peeling (e.g., separating components fastened together via adhesives, tools, etc.).

If a collapsible bag is used, collapsible bag 118 may be fluid tight to enable it to contain a liquid 122, which may contain reactants (e.g., certain solid objects), media, and/or other components necessary for carrying out a desired process such as a chemical, biochemical and/or biological reaction. Collapsible bag 118 may also be configured such that liquid 122 remains substantially in contact only with the collapsible bag during use and is not in contact with support vessel 114. In such embodiments, the bag may be disposable and used for a single reaction or a single series of reactions, after which the bag is discarded. Because the liquid in the collapsible bag in such embodiments does not come into contact with support structure 114, the support structure can be reused without cleaning. That is, after a reaction takes place in container 118, the container can be removed from support structure 114 and replaced by a second (e.g., disposable) container. A second reaction can be carried out in the second container without having to clean either the first container or the reusable support structure.

Figure 3:
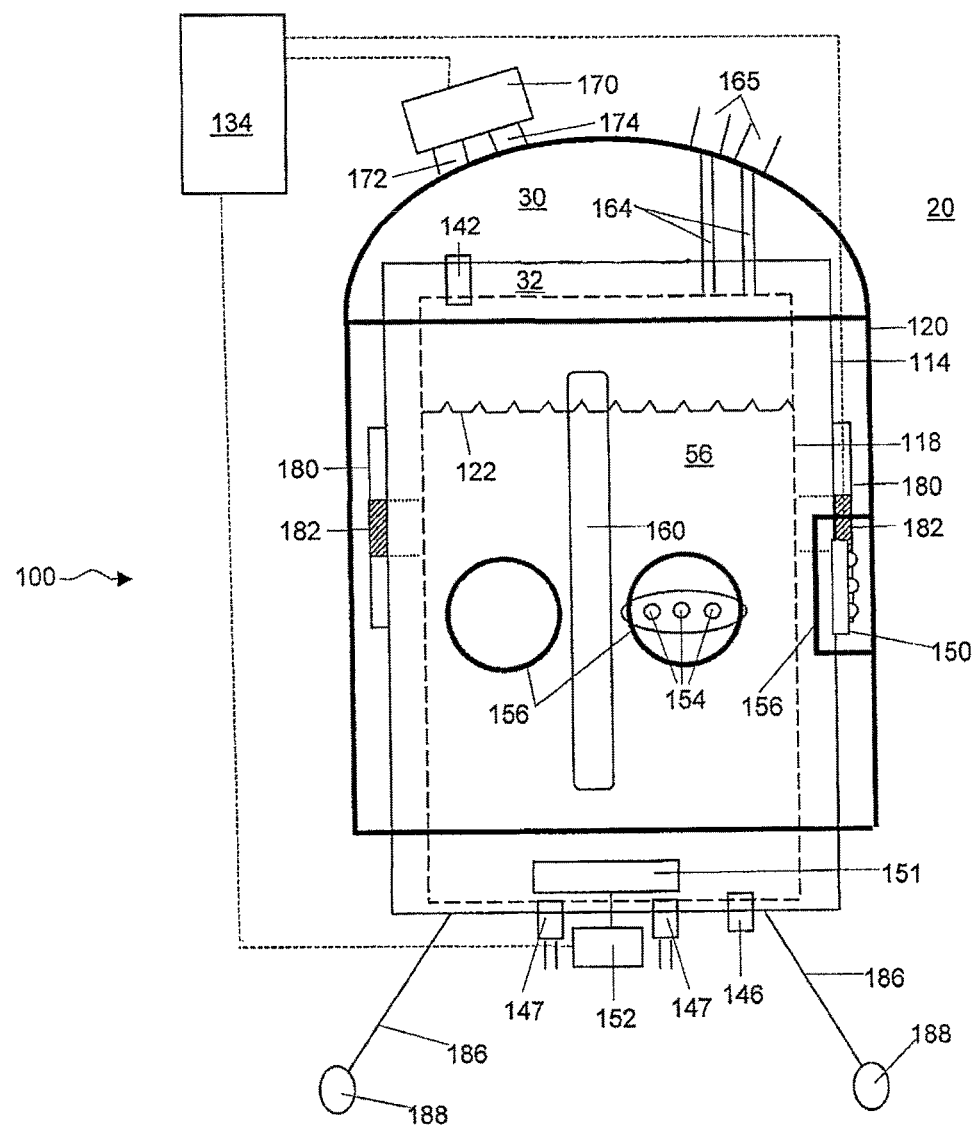
FIG. 3 is a schematic diagram showing an apparatus forming at least a part of a bioreactor system, according to an embodiment of the invention.

Also shown in FIG. 3 are an optional inlet port 142 and optional outlet port 146, which can be formed in container 118 and/or reusable support structure 114 and can facilitate convenient introduction and removal of a liquid and/or gas from the container. The container may have any suitable number of inlet ports and any suitable number of outlet ports. For example, a plurality of inlet ports may be used to provide different gas compositions (e.g., via a plurality of spargers 147), and/or to allow separation of gases prior to their introduction into the container. These ports may be positioned in any suitable location with respect to container 118. For instance, for certain apparatuses including spargers, the container may include one more gas inlet ports located at a bottom portion of the container. Tubing may be connected to the inlet and/or outlet ports to form, e.g., delivery and harvest lines, respectively, for introducing and removing liquid from the container. Optionally, the container and/or support structure may include a utility tower 150, which may be provided to facilitate interconnection of one or more devices internal to the container and/or support structure with one or more pumps, controllers, and/or electronics (e.g., sensor electronics, electronic interfaces, and pressurized gas controllers) or other devices. Such devices may be controlled using a control system 134.

For systems including multiple spargers, control system 134 may be operatively associated with each of the spargers and configured to operate the spargers independently of each other. This can allow, for example, control of multiple gases being introduced into the container. In general, as used herein, a component of a system that is "operatively associated with" one or more other components indicates that such components are directly connected to each other, in direct physical contact with each other without being connected or attached to each other, or are not directly connected to each other or in contact with each other, but are mechanically, magnetically, electrically (including via electromagnetic signals transmitted through space), or fluidically interconnected so as to cause or enable the components so associated to perform their intended functionality.

Apparatus 100 may optionally include a mixing system such as an impeller 151 positioned within container 118, which can be rotated (e.g., about a single axis) using a motor 152 that may be external (or internal) to the container. In some embodiments, as described in more detail below, the impeller and motor are magnetically coupled. In some cases, a base plate is attached (e.g., reversibly or irreversibly) to the container (e.g., a collapsible bag). The base plate may be configured to support an impeller to form an "impeller plate" or "impeller support". The impeller may be attached to or otherwise supported by the base plate by, for example, a shaft, a bearing, and/or by another component. In some cases, the impeller is magnetically actuated and is attached to the base plate via a shaft, a bearing, and/or by another component. The mixing system can be controlled by control system 134. Mixing systems are described in further detail below.

Additionally and/or alternatively, the apparatus may include an antifoaming system such as a mechanical antifoaming device (not shown). The antifoaming device may include, for example, an impeller within container 118 positioned near the top of the container that can be rotated (e.g., magnetically) using a motor, which may be external or internal to the container. The impeller can be used to collapse a foam contained in a head space of the container. In some embodiments, the antifoaming system is in electrical communication with a sensor (e.g., a foam sensor) via a control system. The sensor may determine, for instance, the level or amount of foam in the head space or the pressure in the container, which can trigger regulation or control of the antifoaming system. In other embodiments, the antifoaming system is operated independently of any sensors. Antifoaming systems are described in more detail in a PCT Application entitled, "Gas Delivery Configurations, Foam Control Systems, and Bag Molding Methods and Articles for Collapsible Bag Vessels," filed on Jun. 15, 2007, which is incorporated herein by reference.

Support structure 114 and/or container 118 may also include, in some embodiments, one or more ports 154 that can be used for sampling, analyzing (e.g., determining pH and/or amount of dissolved gases in the liquid), or for other purposes. These ports may be aligned with one or more access ports 156 of optional environmental containment enclosure 120. As shown in the illustrative embodiment, the environmental containment enclosure has a shape and contour that is complementary to a shape and contour of support structure 114 to which the enclosure is attached to allow access to a material contained in the container from various locations around the container. A complementary shaped and contoured environmental containment enclosure can also reduce the overall size and/or footprint of the support structure, container, and environmental containment enclosure combination. This feature is especially well-suited for large containers, where access to ports and/or other components around support structure 114 and/or container 118 may be otherwise difficult. Thus, a user positioned outside of the environmental containment enclosure can access a material within the container via the ports without subjecting the material to an atmosphere 20 surrounding the enclosure. The environmental containment enclosure can prevent or decrease the amount of contamination, e.g., from personnel, equipment, and ambient air, of a material contained in the system and/or the degree of exposure of the material to a user.

As shown, support structure 114 may also include one or more site windows 160 for viewing a level of liquid within the container 118. Alternatively, reusable support structure 114 may be formed of a transparent material to allow visual access into container 118. Environmental containment enclosure 120 may also be formed of a transparent material to allow visual access into the enclosure.

One or more connections 164 may be positioned at a top portion of container 118 or at any other suitable location. Connections 164 may include openings, tubes, and/or valves for adding or withdrawing liquids, gases, and the like from container 118, each of which may optionally include a flow sensor and/or filter (not shown). Optionally, connections 164 may be in fluid communication with gas introduction and withdrawal ports 165.

In some embodiments, one or more connections 172 and 174 may be positioned at a top portion of the environmental containment enclosure 120 or at any other suitable location. Connections 172 and 174 may include openings, tubes, and/or valves for adding or withdrawing gases and the like from the environmental containment enclosure 120, each of which may optionally include a flow sensor and/or filter (not shown). Optionally, connections 172 and 174 can be connected to a ventilation system 170 and may be in fluid communication with the enclosed space defined by gap 130. For instance, connection 172 may be a gas inlet for introducing a gas into the enclosed space and connection 174 may be a gas outlet for removal of a gas from the enclosed space. Ventilation system 170 may include filters (e.g. HEPA filters) and can be configured and operated, under control of control system 134, to create and maintain a sterile, aseptic, substantially particle-free, or reduced-particle environment.

Apparatus 100 may include, in some embodiments, one or more connection ports 180 for interconnecting an interior of reusable support structure 114 (e.g., gap 132) to an interior of a second apparatus. Additionally or alternatively, the apparatus may include one or more connection ports 182 adapted for connecting an interior of container 118 (e.g., interior 56) to an interior of an interior of the second apparatus. These ports can facilitate transfer of a material from interior 56 to the second apparatus or to another suitable container (e.g., a sealed bag). Transfer may be accomplished, for example, by pumping the material through tubing (e.g., by peristaltic pumping or by applying a positive pressure to an inlet), by use of gravity, and/or by application of a vacuum.

The support structure 114 may further include a plurality of supports 186, optionally with wheels 188 for facilitating transport of the apparatus. The supports may include, in some embodiments, load cells that can be used to determine the weight of a liquid inside the container.

It should be understood that not all of the features shown in FIG. 3 need be present in all embodiments of the invention and that the illustrated elements may be otherwise positioned or configured. Also, additional elements may be present in other embodiments, such as the elements described in more detail below.

Various embodiments described herein include a container such as a collapsible bag. "Flexible container", "flexible bag", or "collapsible bag" as used herein, indicates that the container or bag is unable to maintain its shape and/or structural integrity when subjected to the internal pressures (e.g., due to the weight and/or hydrostatic pressure of liquids and/or gases contained therein expected during operation) without the benefit of a separate support structure. The collapsible bag may be made out of inherently flexible materials, such as many plastics, or may be made out of what are normally considered rigid materials (e.g., glass or certain metals) but having a thickness and/or physical properties rendering the container as a whole unable to maintain its shape and/or structural integrity when subjected to the internal pressures expected during operation without the benefit of a separate support structure. In some embodiments, collapsible bags include a combination of flexible and rigid materials; for example, the bag may include rigid components such as connections, ports, supports for a mixing and/or antifoaming system, etc.

A container (e.g., collapsible bag) may have any suitable size for containing a liquid. For example, the container may have a volume between 1-40 L, 40-100 L, 100-200 L, 200-300 L, 300-500 L, 500-750 L, 750-1,000 L, 1,000-2,000 L, 2,000-5,000 L, or 5,000-10,000 L. In some instances, the container has a volume greater than 1 L, or in other instances, greater than 10 L, 20 L, 40 L, 100 L, 200 L, 500 L, or 1,000 L. Volumes greater than 10,000 L are also possible.

In some embodiments, the collapsible bag is disposable and is formed of a suitable flexible material. The flexible material may be one that is USP Class VI certified, e.g., silicone, polycarbonate, polyethylene, and polypropylene. Non-limiting examples of flexible materials include polymers such as polyethylene (e.g., linear low density polyethylene and ultra low density polyethylene), polypropylene, polyvinylchloride, polyvinyldichloride, polyvinylidene chloride, ethylene vinyl acetate, polycarbonate, polymethacrylate, polyvinyl alcohol, nylon, silicone rubber, other synthetic rubbers and/or plastics. As noted above, portions of the flexible container may comprise a substantially rigid material such as a rigid polymer (e.g., high density polyethylene), metal, and/or glass (e.g., in areas for supporting fittings, etc.). In other embodiments, the container is made of a substantially rigid material. All or portions of the container may be optically transparent to allow viewing of contents inside the container. The materials or combination of materials used to form the container may be chosen based on one or more properties such as flexibility, puncture strength, tensile strength, liquid and gas permeabilities, opacity, and adaptability to certain processes such as blow molding, injection molding, or spin cast molding (e.g., for forming seamless collapsible bags).

A container (e.g., collapsible bag) may have any suitable thickness for holding a liquid and may be designed to have a certain resistance to puncturing during operation or while being handled. For instance, the walls of a container may have a total thickness of less than or equal to 250 mils (1 mil is 25.4 micrometers), less than or equal to 200 mils, less than or equal to 100 mils, less than or equal to 70 mils (1 mil is 25.4 micrometers), less than or equal to 50 mils, less than or equal to 25 mils, less than or equal to 15 mils, or less than or equal to 10 mils. In some embodiments, the container includes more than one layer of material that may be laminated together or otherwise attached to one another to impart certain properties to the container. For instance, one layer may be formed of a material that is substantially oxygen impermeable. Another layer may be formed of a material to impart strength to the container. Yet another layer may be included to impart chemical resistance to fluid that may be contained in the container. It should be understood that a container may be formed of any suitable combinations of layers. The container (e.g., collapsible bag) may include, for example, 1 layer, greater than or equal to 2 layers, greater than or equal to 3 layers, or greater than or equal to 5 layers of material(s). Each layer may have a thickness of, for example, less than or equal to 200 mils, less than or equal to 100 mils, less than or equal to 50 mils, less than or equal to 25 mils, less than or equal to 15 mils, less than or equal to 10 mils, less than or equal to 5 mils, or less than or equal to 3 mils, or combinations thereof.

In one set of embodiments of the invention, the container is seamless. The container may be, for example, a seamless collapsible bag or a seamless rigid (or semi-rigid) container. Many existing collapsible bags are constructed from two sheets of a plastic material joined by thermal or chemical bonding to form a container having two longitudinal seams. The open ends of the sheets are then sealed using known techniques and access apertures are formed through the container wall. During use, collapsible bags having seams can cause the formation of crevices at or near the seams where fluids or reagents contained therein are not thoroughly mixed. In certain embodiments involving, for example, the use of collapsible bags for performing a chemical, biochemical and/or biological reaction, unmixed reagents can cause a reduction in yield of a desired product. The presence of seams in a collapsible bag can also result in the inability of the collapsible bag to conform to the shape of a reusable support structure that may support the bag. By using collapsible bags without any seams joining two or more flexible wall portions of the bag, however, the problems of mixing and conformity may be avoided or reduced. In certain embodiments, seamless collapsible bags can be made specifically to fit a particular reusable support structure having a unique shape and configuration. Substantially perfect-fitting collapsible bags can be used, for example, as part of a bioreactor system or a biochemical and/or chemical reaction system. Seamless rigid or semi-rigid containers may also be beneficial in some instances.

In one embodiment, a seamless collapsible bag is formed in a process in which the bag liner (e.g., the flexible wall portions of the bag), as well as one or more components such as a component of an agitator/mixer system (e.g., a shaft and/or a support base), port, etc. is cast from one continuous supply of a polymeric precursor material. In some cases, the casting may occur without hermetically sealing, e.g., via welding. Such a seamless collapsible bag may allow the interior liquid or other product to contact a generally even surface, e.g., one which does not contain substantial wrinkles, folds, crevices, or the like. In addition, in some cases, the collapsible bag complementarily fits within a support structure when installed and filled with a liquid or product. The seamless collapsible bag may also have a generally uniform polymeric surface chemistry which may, for example, minimize side reactions. Methods of forming seamless collapsible bags involving more than one polymeric precursor materials can also be performed.

Seamless collapsible bags can be created by a variety of methods. In one embodiment, a seamless collapsible bag is formed by injecting liquid plastic into a mold that has been pre-fitted with components such as ports, connections, supports, and rigid portions configured to support a mixing system (e.g., a shaft and/or a base) that are subsequently surrounded, submerged, and/or embedded by the liquid plastic. The component may be a rigid component, e.g., one that can substantially maintain its shape and/or structural integrity during use. Any suitable number of components (e.g., at least 1, 2, 5, 10, 15, etc.) can be integrated with containers (e.g., collapsible bags) using methods described herein. The mold may be designed to form a collapsible bag having the shape and volume of the mold, which may have a substantially similar shape, volume, and/or configuration of a reusable support structure.

In one embodiment, a container is formed by using an embedded component/linear molding (ECM) technique. In one such technique, rigid or pre-made components such as tube ports, agitator bases, etc. are first positioned in the mold. A polymer or polymer precursor used to form a container (e.g., a seamless collapsible bag) may be introduced (e.g., in a melt state) via a polymer fabrication technique such as those described below. In some cases, a component or a portion of the component is partially melted by the polymer precursor, allowing the component to form a continuous element with the container. That is, the component can be joined (e.g., fused) with one or more wall portions of the container (e.g., flexible wall portions of a collapsible bag) to form a single, integral piece of material without seams. Such a technique may be used to form, for example, a shaft associated with a base plate that is integrally attached to a collapsible bag and/or a base plate without a shaft that is integrally attached to the collapsible bag.

In certain embodiments, especially in certain embodiments involving fluid manipulations or carrying out a chemical, biochemical and/or biological reaction in a vessel, the vessel is substantially closed, e.g., the vessel is substantially sealed from the environment outside of the container except, in certain embodiments, for one or more inlet and/or outlet ports that allow addition to, and/or withdrawal of contents from, the vessel. If a collapsible bag is used, it may be substantially deflated prior to being filled with a liquid, and may begin to inflate as it is filled with liquid. In other embodiments, aspects of the invention can be applied to opened vessel systems.

In some cases, liquids may be introduced and/or removed from an apparatus, vessel, container, or unit operation component via inlet ports and/or outlet ports. The apparatus or vessel may be a part of or in the form of a reactor system for performing a biological, biochemical, or chemical reaction, or may be in the form of a unit operation component such as a filtration system, seed culture expansion system, primary recovery system, chromatography system, filling system, closed media/buffer preparation system, and water purification system, for example. The apparatus or vessel may have any suitable number of inlet ports and any suitable number of outlet ports. In some cases, pumps, such as disposable pumps, may be used to introduce a gas or other fluid into the vessel, e.g., via an inlet port, and/or which may be used to remove a gas or other fluid from the vessel, e.g., via an outlet port.

In certain embodiments, an apparatus or vessel may be in the form of a support structure, for example, vessel 114 as shown in FIG. 3, which can surround and contain container 118. The support structure may have any suitable shape able to surround and/or contain the container. In some embodiments, the shape of the support structure is substantially similar to the shape of the container. Additionally, one or more walls of the container may conform to and/or lie up against the walls of the support structure. For example, all or a portion the support structure may surround the container, including one or more side portions, top portions, and/or bottom portions of the container. In some instances, the support structure may be configured such that at least 50%, at least 60%, at least 75%, at least 90%, or at least 95% of the external surface area of the container is enclosed by the support structure.

In some cases, the support structure is reusable. The support structure may be formed of a substantially rigid material. Non-limiting examples of materials that can be used to form the reusable support structure include stainless steel, aluminum, glass, resin-impregnated fiberglass or carbon fiber, polymers (e.g., high-density polyethylene, polyacrylate, polycarbonate, polystyrene, nylon or other polyamides, polyesters, phenolic polymers, and combinations thereof. The materials may be certified for use in the environment in which it is used. For example, non-shedding materials may be used in environments where minimal particulate generation is required.

In some embodiments, the reusable support structure may be designed to have a height and diameter similar to standard industrial size stainless steel bioreactors (or other standard reactors or vessels). The design may also be scaleable down to small volume bench reactor systems. Accordingly, the reusable support structure may have any suitable volume for carrying out a desired chemical, biochemical and/or biological reaction. In many instances, the reusable support structure has a volume substantially similar to that of the container. For instance, a single reusable support structure may be used to support and contain and single container having a substantially similar volume. In other cases, however, a reusable support structure is used to contain more than one container. The reusable support structure may have a volume between, for example, 1-100 L, 100-200 L, 200-300 L, 300-500 L, 500-750 L, 750-1,000 L, 1,000-2,000 L, 2,000-5,000 L, or 5,000-10,000 L. In some instances, the reusable support structure has a volume greater than 1 L, or in other instances, greater than 10 L, 20 L, 40 L, 100 L, 200 L, 500 L, or 1,000 L. Volumes greater than 10,000 L are also possible.

In other embodiments, however, an apparatus or vessel described herein does not include a separate container (e.g., collapsible bag) and support structure, but instead comprises a self-supporting disposable or reusable container. The container may be, for example, a plastic vessel and, in some cases, may include an agitation system integrally, irreversibly, or removably attached thereto. The agitation system may be disposable along with the container. In one particular embodiment, such a system includes an impeller welded or bolted to a polymeric container. It should therefore be understood that many of the aspects and features of the vessels described herein with reference to a container and a support structure (for example, a seamless container, a sparging system, an antifoaming device, etc.), are also applicable to a self-supporting disposable container.

Furthermore, an apparatus or vessel may include various sensors and/or probes for controlling and/or monitoring one or more process parameters inside the apparatus or vessel such as, for example, temperature, pressure, pH, dissolved oxygen (DO), dissolved carbon dioxide ($DCO_2$), mixing rate, and gas flow rate. The sensor may also be an optical sensor in some cases.

In some embodiments, process control may be achieved in ways which do not compromise the sterile barrier established by a vessel, container, or environmental containment enclosure. For example, gas flow may be monitored and/or controlled by a rotameter or a mass flow meter upstream of an inlet air filter. In another embodiment, disposable optical probes may be designed to use "patches" of material containing an indicator dye which can be mounted on the inner surface of the disposable container and read through the wall of the disposable container via a window in the reusable support structure. For example, dissolved oxygen, pH, and/or $CO_2$ each may be monitored and controlled by an optical patch and sensor mounted on, e.g., a gamma-irradiatable, biocompatible polymer which, can be sealed to, embedded in, or otherwise attached to the surface of the container.

An apparatus or vessel may be operatively associated with a temperature controller which may be, for example, a heat exchanger, a closed loop water jacket, an electric heating blanket, or a Peltier heater. Other heaters for heating a liquid inside a vessel are known to those of ordinary skill in the art and can also be used in combination with apparatuses described herein. The heater may also include a thermocouple and/or a resistance temperature detector (RTD) for sensing a temperature of the contents inside the vessel. The thermocouple may be operatively connected to the temperature controller to control temperature of the contents in the vessel. Optionally, a heat-conducting material may be embedded in the surface of the vessel to provide a heat transfer surface to overcome the insulating effect of the material used to form other portions of the vessel.

Cooling of an apparatus may also be provided by a closed loop water jacket cooling system, a cooling system mounted on the apparatus, or by standard heat exchange through a cover/jacket associated with an apparatus, for example, on a reusable support structure (e.g., the heat blanket or a packaged dual unit which provides heating and cooling may a component of a device configured for both heating/cooling but may also be separate from a cooling jacket). Cooling may also be provided by Peltier coolers. For example, a Peltier cooler may be applied to an exhaust line to condense gas in the exhaust air to help prevent an exhaust filter from wetting out. In some cases, a coolant such as ethylene glycol or other liquid that can be cooled to a low temperature can be used in a cooling device.

In certain embodiments, an apparatus includes gas cooling for cooling the head space and/or exit exhaust. For example, jacket cooling, electrothermal and/or chemical cooling, or a heat exchanger may be provided at an exit air line and/or in the head space of a container. This cooling can enhance condensate return to the container, which can reduce exit air filter plugging and fouling. In some embodiments, purging of precooled gas into the head space can lower the dew point and/or reduce water vapor burden of the exit air gas.

In some cases, sensors and/or probes may be connected to a sensor electronics module, the output of which can be sent to a terminal board and/or a relay box. The results of the sensing operations may be input into a computer-implemented control system (e.g., a computer) for calculation and control of various parameters (e.g., temperature and weight/volume measurements) and for display and user interface. Such a control system may also include a combination of electronic, mechanical, and/or pneumatic systems to control heat, air, and/or liquid delivered to or withdrawn from the disposable container as required to stabilize or control the environmental parameters of the process operation. It should be appreciated that the control system may perform other functions and the invention is not limited to having any particular function or set of functions.

The one or more control systems described herein can be implemented in numerous ways, such as with dedicated hardware and/or firmware, using a processor that is programmed using microcode or software to perform the functions recited above or any suitable combination of the foregoing. A control system may control one or more operations of a single reactor for a biological, biochemical or chemical reaction, or of multiple (separate or interconnected) reactors.

Each of systems described herein, and components thereof, may be implemented using any of a variety of technologies, including software (e.g., C, C#, C++, Java, or a combination thereof), hardware (e.g., one or more application-specific integrated circuits), firmware (e.g., electrically-programmed memory) or any combination thereof.

Various embodiments according to the invention may be implemented on one or more computer systems. These computer systems, may be, for example, general-purpose computers such as those based on Intel PENTIUM-type and XScale-type processors, Motorola PowerPC, Motorola DragonBall, IBM HPC, Sun UltraSPARC, Hewlett-Packard PA-RISC processors, any of a variety of processors available from Advanced Micro Devices (AMD) or any other type of processor. It should be appreciated that one or more of any type of computer system may be used to implement various embodiments of the invention. The computer system may include specially-programmed, special-purpose hardware, for example, an application-specific integrated circuit (ASIC). Aspects of the invention may be implemented in software, hardware or firmware, or any combination thereof. Further, such methods, acts, systems, system elements and components thereof may be implemented as part of the computer system described above or as an independent component.

In one embodiment, a control system operatively associated with an apparatus or vessel described herein is portable. The control system may include, for example, all or many of the necessary controls and functions required to perform a fluidic manipulation (e.g., mixing and reactions) in the control system. The control system may include a support and wheels for facilitating transport of the vessel. Advantageously, such a portable control system can be programmed with set instructions, if desired, transported (optionally with the vessel), and hooked up to a vessel, ready to perform a fluid manipulation in a shorter amount of time than conventional fluid manipulation control systems (e.g., less than 1 week, 3 days, 1 day, 12 hours, 6 hours, 3 hours, or even less than 1 hour).

An apparatus, including a vessel, may also be connected to one or more sources of gases such as air, oxygen, carbon dioxide, nitrogen, ammonia, or mixtures thereof. The gases may be compressed, pumped, etc. Such gases may be used to provide suitable growth and/or reaction conditions for producing a product inside the vessel. The gases may also be used to provide sparging to the contents inside the vessel, e.g., for mixing or other purposes. For instance, in certain embodiments employing spargers, bubble size and distribution can be controlled by passing an inlet gas stream through a porous surface prior to being added to the vessel. Additionally, the sparging surface may be used as a particulate or solid object (e.g., cell) separation device by alternating pressurization and depressurization (or application of vacuum) on the exterior surface of the porous surface, or by any other suitable method.

In one embodiment, an apparatus, include a vessel or container, is connected to various sources of gases and the inlet gases may optionally pass through a filter, a flow meter, and/or a valve, which may be controlled by controller system, prior to entering the apparatus. The valve may be a pneumatic actuator (actuated by, e.g., compressed air/carbon dioxide or other gas), which may be controlled by a solenoid valve. These solenoid valves may be controlled by a relay connected to terminal board, which is connected to the controller system. The terminal board may comprise, for example, a PCI terminal board, or a USB/parallel, or fire port terminal board of connection. In other embodiments, flush closing valves can be used for addition ports, harvest and sampling valves. Progressive tubing pinch valves that are able to meter flow accurately can also be used. In some cases, the valves may be flush closing valves (e.g., for inlet ports, outlet ports, sampling ports, etc.). The inlet gases may be connected to any suitable inlet of the apparatus. In one embodiment, the inlet gases are associated with one or more spargers which can be controlled independently, as described in more detail below.

As shown in the exemplary embodiment illustrated in FIG. 3, an apparatus comprising a container can be operatively associated with a variety of components as part of an overall apparatus 100. Accordingly, the container and/or support structure may include several fittings to facilitate connection to functional component such as filters, sensors, and mixers, as well as connections to lines for providing reagents such as liquid media, gases, and the like. The container and the fittings may be sterilized prior to use so as to provide a "sterile envelope" protecting the contents inside the container from airborne contaminants outside. In some embodiments, the contents inside the container do not contact the reusable support structure and, therefore, the reusable support structure can be reused after carrying out a particular chemical, biochemical and/or biological reaction without being sterilized, while the container and/or fittings connected to the container can be discarded. In other embodiments, the container, fittings, and/or reusable support structure may be reused (e.g., after cleaning and sterilization).

An apparatus or vessel may also include, in some embodiments, a mixing system for mixing contents of a container and/or an antifoaming system for removing or reducing foam in a headspace of the container. The mixing and/or antifoaming system may include an agitator or mixer. In some cases, more than one agitator or mixer may be used, and the agitators and/or mixers may the same or different. More than one agitation system may be used, for example, to increase mixing power. In some cases, the agitator may be one in which the height can be adjusted, e.g., such that the draft shaft allows raising of an impeller or agitator above the bottom of the tank and/or allows for multiple impellers or agitators to be used. A mixing system of a vessel may be disposable or intended for a single use (e.g., along with the container), in some cases.

Various methods for mixing fluids can be implemented in a container. For instance, mixers based on magnetic actuation, sparging, and/or air-lift can be used. Direct shaft-drive mixers that are sealed and not magnetically coupled can also be used. In one particular embodiment, mixing systems such as the ones disclosed in U.S. patent application Ser. No. 11/147,124, filed Jun. 6, 2005, entitled "Disposable Bioreactor Systems and Methods," by G. Hodge, et al., published as U.S. Patent Application Publication No. 2005/0272146 on Dec. 8, 2005, and a PCT Application entitled, "Gas Delivery Configurations, Foam Control Systems, and Bag Molding Methods and Articles for Collapsible Bag Vessels," filed on Jun. 15, 2007, each of which is incorporated herein by reference in its entirety, are used with embodiments described herein. For example, the mixing system may include a motor, e.g., for driving an impeller (or other component used for mixing) positioned inside the container, a power conditioner, and/or a motor controller.

In some cases, a plurality (e.g., more than 1, 2, or 3, etc.) of mixers or impellers are used for mixing contents in a container (e.g., a collapsible bag). Additionally or alternatively, a mixing system may include an adjustable height impeller and/or an impeller with varying impeller blade configurations. For instance, the mixer may have an extended drive shaft which allows the impeller to be raised to different heights relative to the bottom of the container. The extended shaft can also allow integration of multiple impellers. In another embodiment, a bioreactor system includes more than one agitation drive per container, which can increase mixing power.

To enhance mixing efficiency, a container may include baffles such as internal film webs or protrusions, e.g., positioned across the inside of the container or extending from the inner surface of the container at different heights and at various angles. The baffles may be formed of in any suitable material such as a polymer, a metal, or a ceramic so long as they can be integrated with the container. In some embodiments, the baffles are reversibly or irreversibly attached to a collapsible bag. In other embodiments, the baffles are reversibly or irreversibly attached to a reusable support structure.

In one embodiment, a direct drive agitator is used. Typically, the agitator includes a direct shaft drive that is inserted into the container. In certain instances, the location where the shaft exits the container may be maintained in a sterile condition. For instance, internal and/or external rotating seals may be used to maintain a sterile seal, and/or live hot steam may be used to facilitate maintenance of the sterile seal. By maintaining such a sterile seal, contamination caused by the shaft, e.g., from the external environment, from the exiting gases, etc., may be reduced or avoided.

In another embodiment, a magnetic agitator is used. Typically, a magnetic agitator uses magnets such as fixed or permanent magnets to rotate or otherwise move the agitator, for example, impellers, blades, vanes, plates, cones, etc. In some cases, the magnets within the magnetic agitator are stationary and can be turned on or activated in sequence to accelerate or decelerate the agitator, e.g., via an inner magnetic impeller hub. As there is no penetration of the container by a shaft, there may be no need to maintain the agitator in a sterile condition, e.g., using internal and/or external rotating seals, live hot steam, or the like.

In yet another embodiment, an electromechanical polymeric agitator is used, e.g., an agitator that includes an electromechanical polymer-based impeller that spins itself by "paddling," i.e., where the agitator is mechanically flapped to propel the agitator or impeller, e.g., rotationally.

Figure 4A:
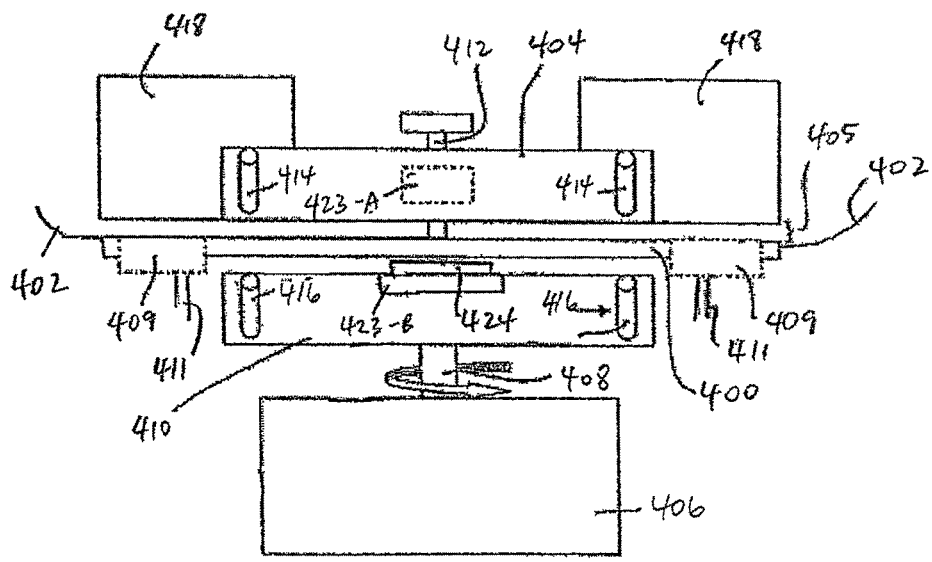
FIGS. 4A-4B illustrate various impeller-comprising mixing devices, according to an embodiment of the invention.
Figure 4B:
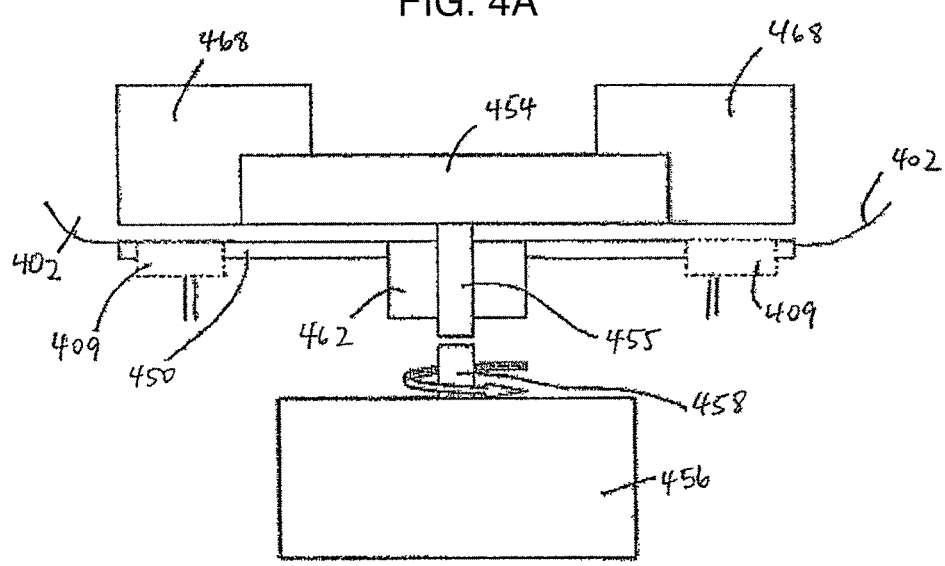
Figure 5:
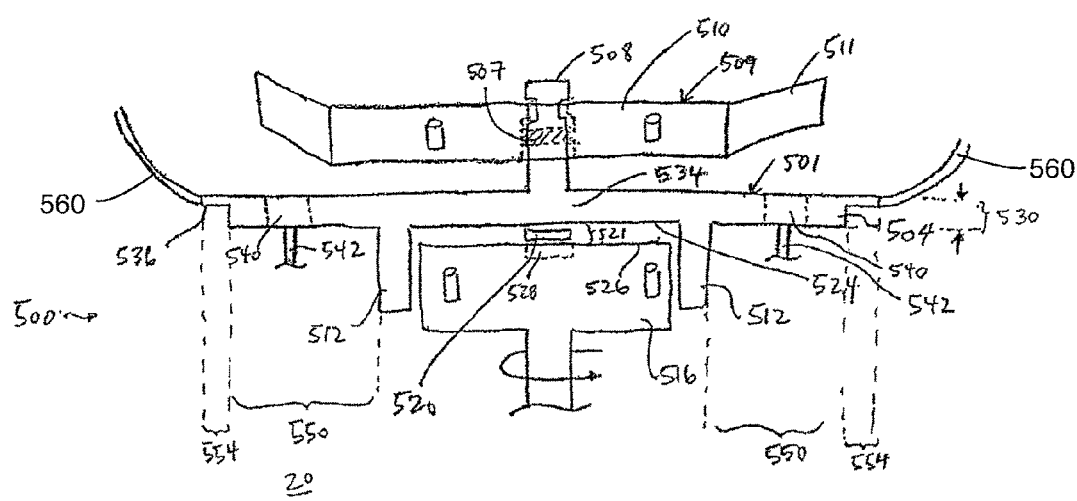
FIG. 5 shows an impeller magnetically coupled to an external motor, according to an embodiment of the invention.
Figure 6:
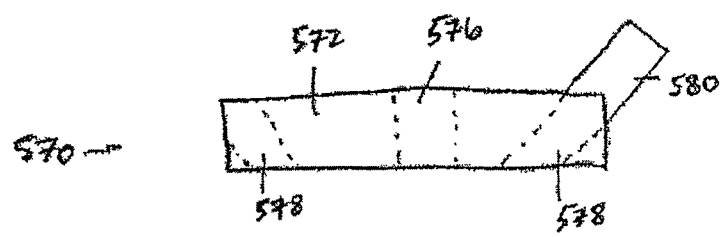
FIG. 6 shows an impeller, according to an embodiment of the invention.

Specific non-limiting examples of devices that can be used as a mixing system, and/or an antifoaming system in certain embodiments, are illustrated in FIGS. 4-6. The devices shown include a magnetically-actuated impeller, although other arrangements are possible. In some of these magnetic configurations, the motor is not directly connected to the impeller. Magnets associated with a drive head can be aligned with magnets associated with an impeller hub, such that the drive head can rotate the impeller through magnetic interactions. In some cases, the motor portion (and other motor associated components) may be mounted on the support structure.

As shown in the embodiment illustrated in FIG. 4A, this exemplary system generally includes an impeller support 400 (e.g., a base plate or impeller plate) affixed to portions of a container wall 402 (e.g., a collapsible bag) at a lower portion thereof, an impeller hub 404, a motor 406, a motor shaft 408 and a drive head 410. The impeller support may be affixed to the wall of the container using any suitable technique, e.g., by heat welding together two portions of a two-piece impeller support, sandwiching the container wall therebetween or onto the wall, or using other methods described herein. As one example, an opening in the wall of the container may be used to allow a central portion of the impeller plate to extend from an exterior of the container to the interior (or vise versa). Then a sealing ring (not shown) may be adhered or the container may be welded directly to an outer circumference of the impeller support to seal the container wall therebetween. As another example, an undersized opening in the wall of the container may be used to form a seal with a circumferential edge of the impeller support slightly larger than the opening. In other embodiments, at least a portion of the impeller support is embedded with a wall of the container and/or the impeller support and container are fabricated simultaneously (e.g., by spin casting, injection molding, or blow molding).

In some embodiments, one or more spargers is associated with an impeller support, which may be used to direct air or other gases into the container. In some cases, the sparger may include porous, micro-porous, or ultrafiltration elements 409 (e.g., sparging elements). The spargers may be used to allow a gaseous sparge or fluids into and/or out of the container by being dimensioned for connection to a source of a gas; this connection may take place via tubing 411. Such sparging and/or fluid addition or removal may be used, in some cases, in conjunction with a mixing system (e.g., the rotation of the impeller hub). Sparging systems are described in more detail below.

In the embodiment illustrated in FIG. 4A, the interior side of the impeller support may include a shaft or post 412 to which a central opening in the impeller hub 404 receives. The impeller hub may be maintained at a slight distance 405 above the surface of the impeller support (e.g., using a physical spacer) to prevent friction therebetween. Low friction materials may be used in the manufacture of the impeller hub to minimize friction between the impeller hub and the post. In another embodiment, one or more bearings may be included to reduce friction. For instance, the impeller hub may include, in certain instances, a bearing 423-A (e.g., a roller bearing, ball bearing (e.g., a radial axis ball bearing), thrust bearing, race bearing, double raceway bearing, lazy-susan bearing, or any other suitable bearing) for reducing or preventing friction between the impeller support and the post. Additionally, the drive head may include a bearing 423-B, the same as or different from bearing 423-A, and/or a physical spacer 424 for reducing or preventing friction between the drive head and the impeller support.

The impeller hub also may include one or more magnets 414, which may be positioned at a periphery of the hub or any other suitable position, and may correspond to a position of a magnet(s) 416 provided on the drive head 410. The poles of the magnets may be aligned in a manner that increases the amount of magnetic attraction between the magnets of the impeller hub and those of the drive head.

The drive head 410 may be centrally mounted on a shaft 408 of motor 406. The impeller hub also may include one or more impeller blades 418. In some cases, the embedded magnet(s) in the impeller can also be used to remove ferrous or magnetic particles from solutions, slurries, or powders.

Further examples of mixing systems are described in more detail in U.S. patent application Ser. No. 11/147,124, filed Jun. 6, 2005, entitled "Disposable Bioreactor Systems and Methods," by G. Hodge, et al., published as U.S. Patent Application Publication No. 2005/0272146 on Dec. 8, 2005, which is incorporated herein by reference.

FIG. 4B illustrates another embodiment, having a mechanically-driven impeller. As shown, this embodiment generally includes an impeller support 450, an impeller hub 454 with shaft 455, and an external motor 456 with shaft 458. The connection of shafts between the impeller hub shaft and the motor shaft may be accomplished in a matter familiar to one of ordinary skill in the art (e.g., gear box, hex drive, or the like).

The impeller support can be affixed, for instance, to a side of container wall 402 at a lower portion thereof. The impeller support may be affixed to the wall of a container by any of the methods described herein. Porous, micro-porous, or ultrafiltration elements 409 may also be included in the present embodiment to allow gaseous sparge or fluids into and out of the bioreactor, as discussed in detail below. In the embodiment illustrated in FIG. 4B, the shaft of the impeller hub may be received in a seal 462 (which may also include a bearing, in some cases) centrally located in an impeller support 450. The seal can be used to prevent or reduce contamination of the contents of the container. The impeller hub can also be maintained at a slight distance above the surface of the impeller support to prevent friction therebetween. The impeller hub may include one or more impeller blades 468, or other suitable mixing structures, such as vanes, plates, cones, etc. Careful and close alignment, vertically and horizontally, between the drive head and impeller support can add significant benefits to mixing devices described herein.

Referring now to FIG. 5, one embodiment of a drive head magnetically coupled to an impeller is illustrated schematically. In FIG. 5, a system 500 including an impeller support 501, shown in a cross-section, includes a substantially horizontal portion 504, from which a substantially vertical impeller shaft 508 extends upwardly supporting an impeller 509 (which may include a core 510 and blades 511). Impeller 509 may rotate about shaft 508. Optionally, this rotation may be facilitated by a bearing 507, which may be any suitable bearing such as a roller bearing, ball bearing (e.g., a radial axis ball bearing), thrust bearing, race bearing, double raceway bearing, lazy-susan bearing, or the like. Impeller support 501 includes drive head alignment elements 512 which, in the embodiment illustrated, are substantially vertical downwardly-depending ridges which can define a circular recess into which at least a portion of a drive head 516 can be inserted. Guide elements 512 are positioned such that drive head, when engaged with the impeller support, position the drive head at a predetermined desired location relative to impeller 509. In one arrangement, guide elements 512 center the drive head, when engaged with the impeller support, with respect to impeller 509. As a further, optional embodiment, a physical spacer 520 can be provided between drive head 516 and a bottom surface 524 of the impeller support aligned with that portion of the top surface 526 of the drive head at the location at which the drive head is ideally positioned with respect to the impeller support. Physical spacer 520 physically separates, by a desired distance, bottom surface 524 of the impeller support with a top surface 526 of the drive head, but, at least one portion between top surface 526 and bottom surface 524 may define a continuous, physical connection (free of voids of air or the like) between the drive head and the impeller support. This allows for closer tolerance of the drive head with the impeller support than would have been realized in many prior arrangements, and it allows for reproducible and secure engagement of the drive head with the impeller support. In some cases, the drive head includes a recess 528 into which at least a portion of physical spacer 520 can be inserted. This arrangement can allow reproducible and secure engagement of the drive head with the physical spacer.

The bottom of the impeller support and the top surface of the drive head can be separated (e.g., using a physical spacer) by a distance 521. In one embodiment, distance 521 is no greater than 50% of average thickness 530 of the substantially horizontal portion 504 of the impeller support. In other embodiments, this distance is no more than 40%, 30%, 20%, 10%, or 5% of the thickness of the impeller support.

In some embodiments, physical spacer 520 has a thickness no greater than 50% of average thickness 530 of the substantially horizontal portion 504 of the impeller support. In other embodiments, this thickness is no more than 40%, 30%, 20%, 10%, or 5% of the thickness of the impeller support.

In one set of embodiments, physical spacer 520 is a bearing that facilitates rotation of the drive head relative to the impeller support. Where physical spacer 520 is a bearing, any suitable bearing can be selected such as a roller bearing, ball bearing (e.g., a radial axis ball bearing), thrust bearing, race bearing, double raceway bearing, lazy-susan bearing, or the like.

In the embodiment illustrated in FIG. 5, the drive head can vary in position, relative to shaft 508, horizontally no more than 5 mm during normal operation or, in other embodiments, no more than 4, 3, 2, 1 (0.5, or 0.25 mm during normal operation). The drive head can also vary in distance relative to bottom surface 524 of the impeller support by no more than 10 mm, 1 mm, 0.5 mm, 0.25 mm, 0.1 mm, or 0.005 mm in certain embodiments with the use of the arrangements illustrated in FIG. 5.

The arrangements of FIG. 5, especially in embodiments where physical spacer 520 is used, also adds physical support to impeller support 501 in addition to any other physical support which the impeller support 501 might receive. This added support is particularly advantageous in collapsible bag arrangements including impellers (e.g., for mixers and/or antifoaming devices).

Optionally, impeller support 501 may include spargers 540 positioned beneath blades of the impeller. The spargers can be dimensioned for connection to one or more sources of gas. For example, the spargers may include a port that can be connected to tubing 542 in fluid communication with one or more sources of gas.

Although figures illustrated herein may show impellers that are positioned at or near a bottom portion of a container, in other embodiments, impellers can be positioned at any suitable location within a container, for example, near the center or a top portion of a container. This can be achieved by extending the length of a shaft which supports the impeller, or by any other suitable configuration. Positions of impellers in a container may depend on the process to be performed in the container. For instance, in some embodiments where sparging is required, impellers may be positioned near the sparger such that the impeller can sweep and/or regulate the bubbles introduced into the container. Additionally, although the figures described herein show a single impeller associated with a shaft, more than one impeller can be used in some instances. For example, a first impeller coupled to a shaft may be located near a bottom portion of the container and a second impeller coupled to the shaft may be positioned near the center of the container. The first impeller may provide adequate sweeping of a sparged gas, and the second impeller may provide adequate mixing of contents within the container.

In some embodiments, the impeller support is uniquely designed to be readily fastenable to a collapsible bag. Certain known arrangements of impellers attached to collapsible bags may suffer from drawbacks resulting from non-ideal attachment of the bag to the impeller support, or non-ideal techniques for such attachment, or both. As shown in the embodiment illustrated in FIG. 5, an impeller support may include a base, substantially perpendicular to a shaft upon which the impeller rotates, having a first portion 534 of a certain average thickness, and a second, peripheral portion 536 thinner and optionally more flexible than the first portion for facilitating attachment to the bag. The first portion thickness is defined as the overall thickness cross-section taken up by the first portion at any point and, where the first portion includes a ribbed or other structure including various thicknesses, the thickness for purposes of this discussion is defined as the thickest portion. The second, peripheral portion, in one embodiment, defines a composition similar to or essentially identical to that of the collapsible bag, and is provided in a thickness similar to that of the collapsible bag. In other embodiments, the second, peripheral portion is formed by a composition different than that of the collapsible bag. For instance, in some embodiments, the first portion is formed in low density polyethylene, and the second portion is formed in high density polyethylene, polypropylene, silicone, polycarbonate, and/or polymethacrylate.

A vessel to which mixing system 500 is associated may support portions of the system such that the system does not break, bend, and/or collapse under the weight of the contents in the vessel. As such, first portion 534 and/or second portion 536 may have suitable average thicknesses and may be formed in suitable materials such that one or both portions are sufficient to adequately support the impeller shaft and/or the support structure itself during use, or under the weight of any contents contained in the vessel. Depending on the size and design of the vessel, in some embodiments, the support structure (e.g., vessel 114 which may be in the form of a reusable support structure) extends under area 554 (e.g., the second portion) to support area 554, leaving area 550 unsupported and exposed to atmosphere 20 outside of the vessel. In such embodiments, second portion 536 may be rigid and/or may be formed in a sufficiently strong material. In other embodiments, the vessel extends under both areas 554 and 550. In some cases, the system may be designed so that much of the strength of the system arises from area 550 of first portion 534. Accordingly, first portion 534 may be rigid and/or may be formed in a sufficiently strong material, while second portion 536 may be flexible and/or unable to support itself under the weight of contents contained in the vessel. In other cases, both the first and second portions can support themselves under the weight of contents contained in the vessel.

The thickness of the peripheral portion of the impeller support and the thickness of the walls of collapsible bag 560, prior to attachment, may differ by no more than 100%, or by no more than 80%, 60%, 40%, 20%, or 10% in other embodiments (e.g., as a percentage of the greater thickness between the walls of the bag and the peripheral portion). Where the thickness of the peripheral portion of the impeller support and the thickness of the disposable bag (at least the portion attachable to the impeller support) are made of similar (or compatible) materials and are of similar thickness, then joining of one to the other can be facilitated easily, reproducibly, and with a product that is free of significant irregularity and thickness in the transition of the bag to the impeller support attachment portion. As described herein, joining of the bag and the support can be performed by any suitable method including, for example, molding and welding (e.g., ultrasonic or heat welding).

In some embodiments, impellers with replaceable blades can be used with apparatuses described herein. FIG. 6 illustrates an impeller 570 that includes a hub 572, which can have a generally circular outer perimeter and may include a center passage 576 before within which the impeller shaft or post (not illustrated) resides. Hub 572 includes one or more slots 578 within which one or more impeller blades 580 can, in some embodiments, be replaceably inserted. As illustrated, one slot 578 is shown not containing a blade and one slot 578 is shown containing an impeller blade. The blade and blade slots are illustrated very schematically and, of course, those of ordinary skill in the art will recognize that a variety of different sizes, shapes, and pitches of blades and slots can be selected by those of ordinary skill in the art for a variety of mixing purposes described herein and known in the art. Blades 580 can be positioned and held within slots 578 securely enough for suitable use and accordance with the invention by any number of techniques including, for example, friction fitting, press fitting, detent mechanism, a clipping and clip release arrangement, fastening with screws, pegs, clamps, or the like, welding (e.g., heat and ultrasonic welding), and use of adhesives.

The replaceable blade arrangement of the invention as illustrated in FIG. 6 provides the advantage in that different blades can be used with a single hub in a mixing/rotating arrangement so that the arrangement can be used for different purposes or involving different rotational speed, torque, mixing profile, or the like. For example, blades of a first size or pitch can be replaced with blades of a second size or pitch to create greater or lesser sheer, aeration, mixing or the like as would be understood by those of ordinary skill in the art. While replaceable blades (e.g., airplane propeller blades) are known in different fields, replaceable blades in a collapsible bag arrangement such as that described herein would not have been expected to have been found based upon knowledge in the art because such bags typically were used only for mixing media containing cells which, to avoid being lysed, must be stirred below a threshold of sheer, or for media containing other materials which can tolerate much higher sheer. However, as described herein, collapsible bag arrangements can be prepared with multiple blades and provided for use with either or both of two or more mixing profiles.

In some cases, the impeller (in some embodiments, via magnetic coupling of the drive head to the impeller) is driven by a motor able to reverse its direction of rotation and/or to be finely tuned with respect to rotational speed. Reversal of direction of spin provides significant advantage in producing a variety of aeration/sparger profiles, or the like. Furthermore, fine tuning of impeller speed can allow for a precise and controllable degree and/or balance of aeration/sparging, sheer, or the like, which has been determined to be quite useful in connection with various media for mixture, especially those including cells. Such embodiments allow for reproducible and controllable adjustment of rotational speed of the impeller that amounts of plus or minus 5% or less through a range of rotational speeds of between 10% and 90% of total maximum impeller rotational speed. In other embodiments, rotational tuning of 4%, 3%, 2%, or 1% of this speed is facilitated. In one arrangement, these aspects are realized by use of a servo motor.

The impeller systems described herein may allow the system to mix liquids, solids, or foams of any type. For example, liquids inside the container may be mixed to provide distribution of nutrients and dissolved gases for cell growth applications. The same disposable container may be used for mixing buffers and media or other solutions in which a disposable product contact surface is desirable. This may also include applications in which the vessel is not required to be sterile or maintain sterility. Moreover, embodiments described herein enable the container holding the fluids/mixtures/gases to be removed and discarded from the reusable support structure such that the reusable support structure is not soiled by the fluids that are mixed in the container. Thus, the reusable support structure need not to be cleaned or sterilized after every use.

In certain embodiments, multiple spargers (including sparging elements) that may be dimensioned for connection to different sources of gas and/or which may be independently controlled are associated with apparatuses described herein. The type of gas, number of spargers, and types and configurations of spargers used in an apparatus (e.g., a bioreactor system or a biochemical/chemical reaction system) may depend, in part, on the particular process to be carried out (e.g., an aerobic versus anaerobic reaction), the removal of any toxic byproducts from the liquid, the control of pH of a reaction, etc. As described in more detail below in connection with certain embodiments described herein, a system may include separate spargers for different gases which may have different functions in carrying out, for example, a chemical, biochemical and/or biological reaction. For instance, a bioreactor system for cell cultivation may include different types of gases such as a "dissolved oxygen (DO) control gas" for controlling the amount of dissolved oxygen in the culture fluid, a "strip gas" for controlling the amount of toxic byproducts in the culture fluid, and a "pH control gas" for controlling the pH of the culture fluid. Each type of gas may be introduced into the culture using different spargers that can be independently operated and controlled. Advantageously, such a system may provide faster process control and less process control variability (compared to, for example, certain systems that combine a DO control gas, strip gas, and pH control gas into one gas stream introduced into a reactor). Chemical, biochemical and/or biological reactions carried out in bioreactor systems described herein may also require lower consumption of gas which can save money on expensive gases, and/or less total gas flow rate (e.g., for a strip gas), which can reduce foam generation and/or reduce the size of inlet gas sterile filters required.

In some embodiments, apparatuses and vessels described herein are a part of a bioreactor system. In bioreactors used for certain types of cell cultivation, cells may require nutrients such as sugars, a nitrogen source (such as ammonia ($NH_3$) or amino acids), various salts, trace metals and oxygen to grow and divide. Like the other nutrients, even and uniform distribution of oxygen throughout the reactor may be essential to provide uniform cell growth. Poor distribution of oxygen can create pockets of cells deprived of oxygen, leading to slower growth, alteration of the cell metabolism or even cell death. In certain applications where the cells are engineered to produce a bioproduct, oxygen deprivation can have a sever affect on the quantity and quality of bioproduct formation. The amount of nutrients available to cells at any one time depends in part on the nutrient concentration in the fluid. Sugars, nitrogen sources, salts, and trace metals may be soluble in fluid and, therefore, may be in excess and readily available to the cells. Oxygen, on the other hand, may be relatively poorly soluble or "dissolved" in water. In addition, the presence of salts plus the elevated temperature necessary to grow cells may further reduce dissolved oxygen concentration. To compensate, a rapid dissolved oxygen sensing system, constant and steady transfer of oxygen into the fluid (e.g., using one or more spargers as described herein), combined with rapid and even distribution in the bioreactor may be used to reduce or prevent oxygen starvation.

Since oxygen transfer from the gas bubbles entering the fluid of the culture may be an important control parameter, the time constant of responsiveness of the gas delivery system may also be important. In certain embodiments, as cell population density increases, the response rate of the gassing system to supply oxygen enriched DO control gas may become increasingly important. Accordingly, in some embodiments, systems described herein include one or more sensors such as a DO sensor which detects the need for more oxygen (or other gas), a gas controller, and one or more spargers which can be signaled to enrich the culture with extra oxygen using, for example, a $N_2/O_2$/air control gas. Since delay time (e.g., several minutes) for this enriched gas to reach the reactor can result in a drop in DO which can lead to oxygen starvation, systems described herein may include a control feedback loop between the sensor(s), gas controller, and sparger(s). Thus, responsive, and even supply and distribution of oxygen-bearing control gas (e.g., a $N_2/O_2$/air mix) may be provided for controlled, predictable cell growth and bioproduct formation. Systems described herein allowing independent control of spargers and/or gas compositions may be advantageous compared to systems that require gases to be flushed out before sparging a different gas into the container.

In addition, since compressed air and oxygen may be expensive to supply to the reactor, a system that provides just enough air enriched with just enough oxygen such that the bubbles are not lost to the head space of the container (and lost out through the exhaust line) may be implemented. This can be performed, for example, by controlling the amount and flow rate of a control gas independently of other gases used in the system (e.g., a strip gas and/or a pH control gas).

Without wishing to be bound by any theory, it is believed that the rate of oxygen transfer into the bioreactor fluid from air, pure oxygen or a gas mixture is directly related to the amount of total surface area of the bubbles in the fluid. Hence, larger bubbles provide less total surface area than a fine mist of very small bubbles. For this reason, in certain embodiments of the invention, a control gas may be provided through microporous spargers to create very small bubbles. A microporous sparger may include apertures having a size (e.g., average diameter) of, for example, less than less than 500 microns, less than 200 microns, less than 100 microns, less than 60 microns, less than 50 microns, less than 40 microns, less than 30 microns, less than 20 microns, less than 10 microns, less than 3 microns, less than about 1 micron, or less than 0.1 microns. In certain embodiments, microporous spargers have an aperture size between 0.1 and 100 microns. Of course, spargers having larger aperture sizes may also be used. For instance, a sparger may have an aperture size between 0.1 and 10 mm. The aperture size may be greater than 100 microns, greater than 200 microns, greater than 500 microns, greater than 1 mm, greater than 3 mm, greater than 5 mm, greater than 7 mm, or greater than 10 mm. The aperture may have any suitable cross-sectional shape (e.g., circular, oval, triangular, irregular, square or rectangular, or the like). Spargers having combinations of aperture sizes can be incorporated into vessels described herein.

Additionally, good cell growth and controlled metabolism may be dependent upon removal of toxic byproducts of cell growth, such as, for example, carbon dioxide, ammonia and volatile organic acids. Carbon dioxide may be highly soluble in water, which can exacerbate its toxic effect on cells. These byproducts can be "stripped" out of the culture fluid by gassing the culture using a strip gas. Accordingly, even distribution of strip gas and strip gas that is introduced at a flow rate sufficiently high enough for bubbles to escape out of the culture (and out the exhaust vent, for example) may be important for cell growth and/or bioproduct production. These parameters may be controlled independently of other gases used in the system (e.g., a control gas and/or a pH control gas) using a separate sparger for the strip gas.

In some instances, a strip gas is introduced into a container using a sparger having an aperture size between 0.1 and 10 mm. For example, the aperture size may be greater than 100 microns, greater than 200 microns, greater than 500 microns, greater than 1 mm, greater than 3 mm, greater than 5 mm, greater than 7 mm, or greater than 10 mm. These aperture sizes can allow relatively larger bubbles to pass through the liquid of the container, which can strip any toxic byproducts out of the liquid without creating large amounts of foam in the head space of the container.

In certain embodiments, a pH control gas is used to control the pH of the fluid in a bioreactor system. For example, carbon dioxide may be used to increase solution pH and ammonia may be used to decrease solution pH. In one embodiment, a pH control gas may include a combination of carbon dioxide, ammonia, or other gases to control (e.g., increase or decrease) pH. In another embodiment, the pH of a reaction fluid is controlled by a first sparger containing an agent that increases pH (e.g., $CO_2$) and a second sparger containing an agent that decreases pH (e.g., $NH_3$).

One or more pH control gases may be added to a container of the bioreactor system upon signals from a pH control sensor associated with the system. The pH control gases may be operated independently and without interference by oxygen demand (e.g., a DO control gas) or strip gas systems. A pH control gas may be introduced into a container using spargers having apertures of various sizes.

In other embodiments, cells that are normally grown without oxygen (e.g., anaerobic reactions) or which are even sensitive to oxygen require removal of oxygen from the culture. Even and controlled distribution of nitrogen gas in these cultures may be used to control proper cell growth and product formation.

As mentioned, in some embodiments described herein, gases such as air, $CO_2$, $O_2$, $N_2$, $NH_3$, and/or dissolved oxygen may be sparged into the container. In some cases, the sparging can be controlled, for instance, such that the sparging can be rapidly activated or altered as needed. Multiple spargers may be used in some cases. For example, in one embodiment, different gas compositions may each be introduced into the container using multiple spargers, e.g., a first sparger for a first gas composition, a second sparger for a second gas composition, a third sparger for a third gas composition, etc. The gases may differ in composition and/or in concentration. As a specific example, a first gas composition may include air with 5% $CO_2$, and a second gas composition may include air with 10% $CO_2$; in another example, a first gas composition may include $O_2$, and a second gas composition may include $N_2$; in yet another example, a first gas composition may include a control gas, a second gas composition may include a strip gas, and a third gas composition may include a pH control gas. Of course, other combinations of gases are also possible. In some cases, multiple spargers may be useful to allow faster responses, e.g., as the gas composition being introduced into the container may be rapidly changed by activating different spargers, e.g., singly and/or in combination. As a specific example, the gas being introduced into a container can be rapidly switched from a first gas (via a first sparger) to a second gas (via a second sparger), and/or to a combination of the first and second gas, or a combination of the second gas and a third gas, etc. The flow rates of each gas can also be changed independently of one another. (In contrast, with a single sparger, a change in composition requires that the new composition reach the sparger before being introduced into the container.) Moreover, the use of multiple spargers can allow customization of the type of sparger for a particular type of gas, e.g., a strip gas, DO control gas, pH control gas, air, $CO_2$, $O_2$, $N_2$, $NH_3$, or any other suitable gas, if desired.

Sparging may be run continuously, periodically, or in some cases, in response to certain events, e.g., within a bioreactor system and/or within the container. For example, as mentioned, the spargers may be connected to one or more sensors and a control system which is able to monitor the amount of sparging, the degree of foaming, the amount or concentration of a substance in the container, and respond by initiating, reducing, or increasing the degree of sparging of one or more composition(s) of gases.

In one particular embodiment, an apparatus or vessel (e.g., as part of a reactor system for performing a biological, biochemical or chemical reaction) is configured to contain a volume of liquid and includes a container (e.g., a collapsible bag) having a volume of at least 2 liters (or any other suitable volume) to contain the volume of the liquid. The vessel may optionally include a support structure for surrounding and containing the container. Additionally, the vessel includes a first sparger connected or dimensioned to be connected to a source of a first gas composition in fluid communication with the container, and a second sparger connected or dimensioned to be connected to a source of a second gas composition different from the first gas composition in fluid communication with the container. The vessel further comprises a control system operatively associated with the first and second spargers and configured to operate the spargers independently of each other. Of course, third, fourth, fifth, or greater numbers of spargers can be included (e.g., greater than 10, or greater than 20 spargers), depending on, for example, the size of the container. In some embodiments, the vessel further comprises a mixing system including an impeller and a base plate, wherein the first and/or second spargers is associated with the base plate. The vessel may be part of an apparatus comprising at least one environmental containment enclosure at least partially surrounding and, optionally, attached to the vessel. In one particular embodiment, the first gas composition comprises air and the second gas composition comprises air supplemented with $O_2$ and $N_2$. If additional spargers are included, the spargers can be connected to a source of gas comprising $N_2$, $CO_2$, $NH_3$ and/or any other suitable gas.

In another exemplary embodiment, an apparatus or vessel configured to contain a volume of liquid comprises a container (e.g., a collapsible bag) to contain the liquid, and optionally, a support structure for surrounding and containing the collapsible bag. The vessel includes a first sparger connected to the container, the first sparger having a first aperture size, wherein at least a portion of the first sparger is dimensioned to be connected to a source of a first gas composition. The vessel also includes a second sparger connected to the container, the second sparger having a second aperture size, wherein at least a portion of the second sparger is dimensioned to be connected to a source of a second gas composition. The second gas composition may have the same or a different composition than the first gas composition. In some embodiments, the vessel is part of a bioreactor system; or, the vessel may be a part of a biochemical/chemical reaction system, or a mixing system. The vessel may include a control system operatively associated with the first and second spargers and may be configured to operate the spargers (or gases associated therewith) independently of each other. The vessel may include any suitable number of spargers (e.g., greater than 10 or greater than 20 spargers), and the container may have any suitable volume (e.g., at least 2, 10, 20, 40, or 100 liters). The first and/or second gas composition(s) may include, for example, $N_2$, $O_2$, $CO_2$, $NH_3$, or air. For example, in one instance, the first gas comprises air and the second gas comprises air supplemented with $O_2$ and $N_2$. The first aperture size may be larger than the second aperture size. For instance, the first aperture size may be between 0.1 and 10 mm, and the second aperture size may be between 0.1 and 100 microns.

Apertures associated with spargers can be formed in any suitable material. For instance, in one embodiment, a porous polymeric material is used as a sparging element to allow transport of gas from one side to another side of the material. Apertures can also be formed in other materials such as metals, ceramics, polymers, and/or combinations thereof. Materials having pores or apertures can have any suitable configuration. For example, the materials may be knitted, woven, or used to form meshes or other porous elements. The elements may be in the form of sheets, films, and blocks, for example, and may have any suitable dimension. In some cases, such elements are incorporated with impellers or impeller supports, e.g., as illustrated in FIG. 5. The elements can be positioned and held within regions of the impeller or impeller support securely enough for suitable use and accordance with the invention by any number of techniques including, for example, friction fitting, press fitting, detent mechanism, a clipping and clip release arrangement, fastening with screws, pegs, clamps, or the like, welding (e.g., heat and ultrasonic welding), and use of adhesives. In other embodiments, portions of the impeller and/or impeller support can be fabricated directly with pores or apertures that can allow fluids to flow therethrough.

In another embodiment, a sparger can be in the form of an open tube/pipe including a plurality of pores (e.g., 5-10 micron diameter holes, or larger holes in other embodiments) for delivering a gas (e.g., a strip gas) to an apparatus. The tube may be straight or curved, and may be rigid, semi-rigid or flexible. In some embodiments, the tube is positioned at a bottom portion of an apparatus; for example, the tube may extend from the bottom of a collapsible bag. However, in other embodiments, other positions are possible. For instance, all or a portion of a tube may be positioned at a side, top, and/or central portion of the apparatus. Multiple open tube spargers may also be used.

In certain embodiments, a combination of different spargers are used in apparatuses described herein. For instance, an apparatus (or collapsible bag) may include one or more spargers in the form of an open tube, as well as one or more spargers that are incorporated into an impeller support. Other configurations of spargers are also possible.

The apparatus or vessel may optionally include one or more sensors in electrical communication with the control system for determining an amount or concentration of a gas (e.g., $O_2$, $N_2$, $CO_2$, $NH_3$, a bi-product of a reaction) in the container. Additionally and/or alternatively, the vessel may include a sensor in electrical communication with the control system for determining a pH of a liquid in the container, or an amount or level of a foam in the container (e.g., bag).

Figure 7:
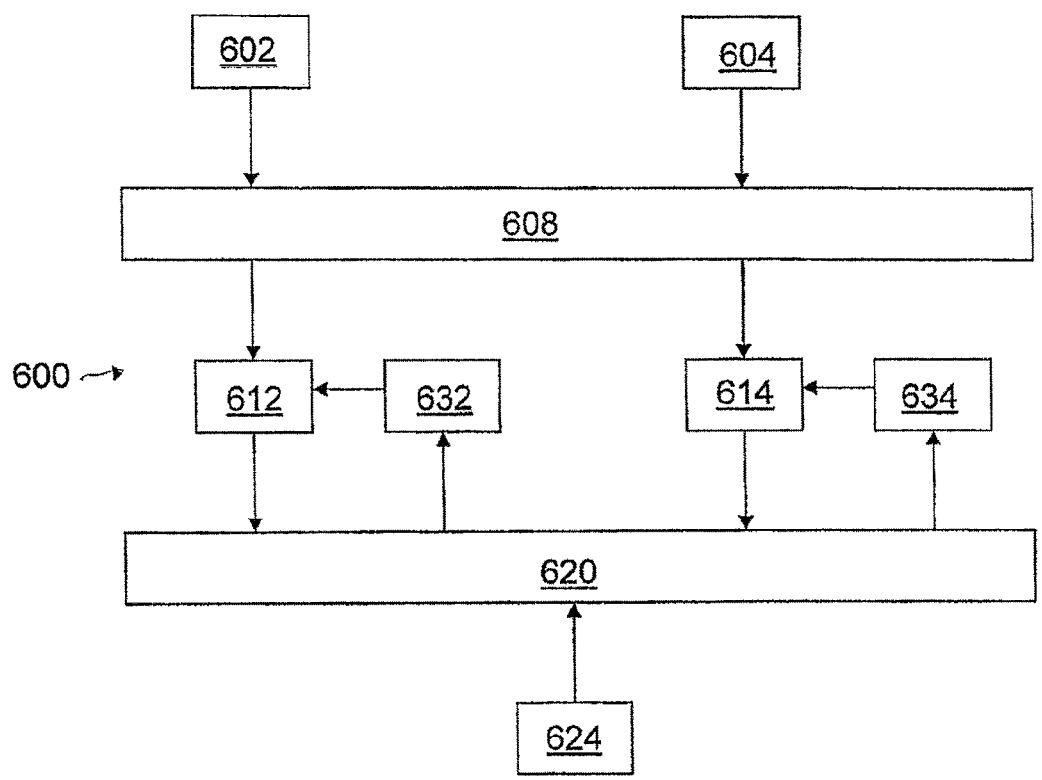
FIG. 7 shows an example of a control and feedback process for operating certain embodiments of the disclosed apparatuses and systems, according to an embodiment of the invention.

As mentioned, control systems and feedback loops may be used to control a variety of processes described herein, including the degree of sparging in one embodiment, or degree of mixing, amount of reagent concentration, or activity of a pump or ventilation system in other embodiments. One example of such a control and feedback process is shown in the embodiment illustrated in FIG. 7. System 600 may include a first sensor 602 (e.g., for detecting the amount and/or concentration of $CO_2$ of a liquid in the container) and a second sensor 604 (e.g., for detecting the amount and/or concentration of $O_2$ of a liquid in the container). After calibrating the sensors, reagents may be added to a container 608 and a fluidic manipulation process, such as mixing or performing a biological, chemical, or biochemical reaction, may be take place. The amount of a gas such as $O_2$ and $CO_2$ may vary in the liquid of the container as the process proceeds. For example, if a biological reaction involving cells takes place, the cells may consume $O_2$ and form $CO_2$ over time, which may vary depending on the growth stage of the cells. Thus, the amount and/or concentration of gases can be determined by the sensors (e.g., as a function of time), and signals 612 and 614 related to the amounts and/or concentrations of the gases can be sent to a control system 620. The control system may include recorded parameters 624, such as threshold levels of one or more gases that can be inputted by a user prior to or during the reaction. For example, a parameter may include a certain threshold level of $CO_2$ in the liquid before a sparger is activated to reduce the amount of $CO_2$ using a strip gas. Accordingly, a signal may be sent from the control system to activate a component 632, such as a valve connected to a source of a strip gas used to reduce the amount of $CO_2$. As the strip gas is introduced into container 608, the amount and/or concentration of $CO_2$ may decrease, which can be measured by 612 and signals sent to the control system. When the amount and/or concentration of $CO_2$ decreases to a certain level, the control system can lower or deactivate the amount of $CO_2$ being introduced into the container, thereby completing the feedback loop. A similar process can take place independently of the process described above using second sensor 614, which may measure, for example, a second gas, a pH, or an amount of a foam in a head space of the container. In other embodiments, a similar process may be performed for measuring the amount of particulate material in an environmental containment enclosure and activation/regulation of an environmental treatment process.

In another embodiment, a feedback process similar to the one described above can be implemented for controlling the amount of a reagent (e.g., glucose) added to the apparatus. For instance, an apparatus used to culture cells (or other organisms) may include one or more sensors for detecting the amount of dissolved oxygen in a liquid contained in the apparatus. As the cells consume glucose, they continue to grow. As the glucose is substantially consumed, the cells slow down their growth and demand less oxygen, which raises the dissolved oxygen level. The sensor can detect (e.g., continuously or periodically) the increased level of dissolved oxygen and this signal can be sent to a control system. Upon reaching a particular high threshold level of dissolved oxygen, which can be pre-programmed into the control system, the control system may send a signal to activate a pump, valve, or other component that is operatively associated with a glucose reservoir. As glucose is added to the liquid in the apparatus, the cells may continue to grow and consume more oxygen, which can be detected by the dissolved oxygen sensor. Upon reaching a certain low threshold level of dissolved oxygen, which can be pre-programmed into the control system, the control system may send a signal to a pump, valve, or other component to decrease the level glucose being added to the apparatus. Advantageously, in apparatuses including feedback for controlling the amount of glucose added, dosing the cells with too much glucose, which can lead to harmful effects in some cases, can be avoided or reduced. A similar system may be used to control the amount of other reagents added to the apparatus during carrying out of a process in the apparatus.

As described herein, a system of the invention can include one or more separation devices. In some cases, a separation device is a liquid-solids separation device, i.e., a device that is configured and arranged to separate solid objects from the liquid with which the objects are associated. In other cases, a separation device described herein separates entities (e.g., proteins) that are dissolved in the liquid.

A separation device may be associated with a system or apparatus of the invention in any suitable manner. In some embodiments, the separation device is positioned in an internal portion of, or a portion of a surface of, a container (e.g., a collapsible bag) or apparatus adapted to contain the liquid and solids to be separated. The separation device may be a part of the structure of the container, e.g., a part of a base plate of a container, in some embodiments. For example, in one such embodiment, porous elements 409 described previously for use as spargers (see FIG. 4A) may comprise a porous media having a pore size and configuration effective for separating cells or other solid objects from liquid upon removal of liquid from the container through the elements 409. In other embodiments, the separation device is external to the container adapted to contain the liquid and solids to be separated; for instance, the separation device may form at least a part of a liquid transfer device/line connecting two apparatuses, or the separation device may form at least a part of a second apparatus in fluid communication with a first apparatus. Combinations of internal and external separation devices can be used and, in some embodiments, multiple separation devices can be placed in series and/or parallel.

Separations may be performed continuously or periodically in systems of the invention. Additionally, as described herein, separation devices may form part of a liquid recycling system (e.g., a loop) with one or more other apparatuses. For example, an outlet of an apparatus, such as a bioreactor, may be in fluid communication with an inlet of the separation device, and an outlet of the separation device may be in fluid communication with an inlet of the apparatus. Such a system may be used to perform continuous perfusion, in some embodiments.

Depending on the particular components to be separated, a variety of separation devices can be implemented with systems described herein. Such systems may be internal or external to a container (e.g., collapsible bag) adapted for containing a liquid. Parameters such as pore size, flow rate, optional cross flow recirculation rate, filtrate rate, and filtrate volume to membrane area ratio can be chosen and/or varied in these and other systems as would be understood by a skilled artisan as needed to meet particular performance objectives. For example, in some embodiments, separation devices can be manipulated to control the concentration of the solid objects passing through various portions of the system. For rotational separation devices (e.g., centrifuges), this can be done, for example, by varying the rpm and thus the G force of the device. The permeate flow rate drawn out of the separation device can also be controlled and pore size can be selected as desired for a particular desired performance result.

In some embodiments, separation devices are in the form of filtration devices. Non-limiting examples of filtration devices include microporous filters, ultrafiltration devices, membrane filters, depth filters, hollow fiber filters, plate and frame filtration devices, tangential flow filters, spinning filters, and the like. An example of a potentially suitable hollow fiber filter is the Amersham Biosciences hollow fiber cartridge (Cat# UFP-500-C-6A, 500K MW cutoff, 0.48 m$^2$, fiber ID 0.5 mm hollow fiber).

In other embodiments, gravity sedimentation can be used to separate solid objects from liquids in apparatuses described herein. Devices such as settling devices, which may be inclined or not inclined, are known in the art and may be used in systems of the invention.

A separation device may also be in the form of a centrifuge, in some embodiments. Although in some cases centrifugation has found limited application in cell culture due to the difficulty in maintaining sterility, one aspect of the invention involves the use of a centrifuge comprising a disposable liner/collapsible bag as part of a system described herein. The liquid-solids mixture may be contained in the disposable liner, which can be supported by a reusable support structure. Accordingly, because the liquid-solids mixture in the liner does not come into contact with the support structure, the support structure can be reused without cleaning. For example, after separation takes place, the liner can be removed from the support structure and replaced by a second (e.g., disposable) liner. A second separation can then be carried out using the second liner without having to clean either the first liner or the reusable support structure. An example of a centrifuge that includes disposable components is the Carr Centritech CELL 1 centrifuge (Item/Part=CELL; Item/Part#=85400).

As described above, in some embodiments, a system of the invention includes a storage tank for storing a liquid (e.g., media, buffer, reagents, or other solutions). The storage tank may be in the form of a collapsible bag, which may optionally be supported by a reusable support structure adapted for surround and containing the collapsible bag. In other embodiments, rigid containers, wherein inner walls of the container are in direct contact with the liquid, can be used as storage tanks.

In some cases, the storage tank is in fluid communication with a mixing system that generates the solution to be stored in the storage tank. In certain such embodiments, one or more sterilized filters may be used to filter the solution prior to or during transfer of solutions into the storage tank. Such a system may generate, for example, filtered media (e.g., which may be suitable for fermentations or for other processes performed in a container) such as growth media and glucose media (including glucose, vitamins, etc.). Advantageously, these and other systems may replace the need for media that is sterilized by autoclaving or steaming in place.

In certain embodiments, a system described herein includes an enclosed resin loading/column packing system. Typically, column packing typically may be accomplished in a clean room with open carboys containing the resin which is manually mixed while the resin slurry is pumped onto the column. In one embodiment, however, a container such as a flexible container is loaded with chromatography resin which is slurried by an agitator while the slurry is pumped into a column.

In another aspect, a bubble column or airlift system (utilizing bubbles of air or other gas) may be used with the disposable bag. Such a system may provide a mixing force by the addition of gas (e.g., air) near the bottom of the reactor. Here, the rising gas bubble and the lower density of gas-saturated liquid rise, displacing gas-poor liquid which falls, providing top-to-bottom circulation. The path of rising liquid can be guided, for example, using dividers inside the chamber of the bag. For instance, using a sheet of plastic which bisects the interior of the bioreactor bag, e.g., vertically, with a gap at the top and the bottom. In some cases, a bag to be used with a reusable support structure comprises such a partition. In other cases, a partition is attached to a reusable support structure. Gas may be added on one side of the divider, causing the gas and gas-rich liquid to rise on one side, cross over the top of the barrier sheet, and descend on the other side, passing under the divider to return to the gas-addition point. In addition, such a bubble column/air-lift mixing system and method may be combined with any of the other mixing systems described herein.

In certain chemical, biochemical and/or biological processes requiring light, an apparatus described herein may include direct, indirect and/or piped-in lighting, e.g., using fiber-optics, according to another aspect of the invention. Any suitable light source may be used. Such apparatuses may be useful for processing, for example, plant cells, e.g., to activate photosynthesis. In one particular embodiment, a phosphorescent flexible container is used to provide light, e.g., for growth of plant cells.

The following example is intended to illustrate certain embodiments of the present invention, but are not to be construed as limiting and do not exemplify the full scope of the invention.

EXAMPLE

This example describes the performance of a microbial perfusion process with a disposable bioreactor system in conjunction with a cell separation device. Specifically, cultivation of the microorganism *E. Coli* was operated in a XDR200™ disposable bioreactor system and cell separation was performed using a hollow fiber cartridge.

The XDR200 bioreactor (having a single frit sparge of nominal 2 micron and the magnetically-driven impeller shown schematically in FIG. 5) was controlled using a Bionet (or PLC) control system. The control parameters of the bioreactor are shown in Table 1. First, a 65 L culture was operated in batch mode until a target culture density, as measured by optical density (O.D.) measurements, reached 5±1 AU and/or a glucose concentration of 5±2 g/L was reached. Then, perfusion was initiated to test the effect of external cell separation/perfusion on cell density, the overall culture performance, and the ability to control the culture glucose concentration at >2 g/L. The cells were returned to the bioreactor via the hollow fiber cartridge retentate flow. The conditioned or spent medium was directed to a waste reservoir from the hollow fiber cartridge permeate flow. Medium from the feed medium system/source was continuously or semi-continuously delivered into the bioreactor at a rate equal to the hollow fiber permeate outflow rate in order to maintain a substantially constant bioreactor or culture volume.

The hollow fiber cartridge used was a GE Healthcare model # UFP-500-C-6A. The cartridge surface area was 4800 cm$^2$ with a nominal lumen i.d. of 0.5 mm. The cartridges were prepared according to manufacturer's recommendations as follows:

1) Purified water flush
2) 20% Ethanol flush and recirculation followed by overnight hold
3) Purified water flush
4) Water flux measurement >399 Lmh/14.5 psi @25° C.
5) Autoclave @ 121° C. for 60 min on liquid cycle A 65 L of feed medium (1 reactor volume/day) equaled a permeate flow rate of 45-50 mL/min. The expected permeate flow rate for this fiber was significantly higher than 50 mL/min; therefore, regulated restriction of the permeate flow rate was necessary, as unrestricted permeate flow could lead to membrane fouling. The permeate was adjusted in order to maintain target culture values. Cross flow was maintained at 10 to 20 times the permeate flow rate, specifically, to achieve a retentate flow rate of 1.4 L/min. The manufacturer's recommended cross flow rate range for this fiber was 1.1-8.6 L/min) and the recommended transmembrane pressure (TMP) was 5-15 psi.

A pump drew culture from the XDR bioreactor to the hollow fiber cartridge. A pressure indicator was positioned between the pump and the cartridge. The transmembrane pressure of the hollow fiber cartridge was maintained at or below approximately 5 psi. This was achieved by adjusting valves or clamps on the retentate outlet and permeate outlet lines of the hollow fiber cartridge, as was necessary. Conditioned medium flowed from the permeate ports of the cartridge and the cells flowed from the retentate returning back to the bioreactor. The feed and retentate lines were adjusted in order to minimize splashing and/or foaming within the bioreactor.

The following protocols were followed to perform E. Coli fermentation seed scale-up in the bioreactor.
1. Remove a vial from the −80° C. freezer and record the data from the label.
2. Thaw the vial at room temperature. Transfer the cells to a 4 mL plastic tube. Incubate on ice for 5 minutes.
3. Heat shock the culture at 42° C. for 45 seconds.
4. Add 800 µL of SOC medium and incubate at 37° C. for 1 hour with constant shaking at 250 rpm.
5. Inoculate a 1000 mL-culture of LB in a 500 mL shake flask with 1 mL of the culture.
6. Incubate for 4-8 hours at 37° C. with constant shaking at 250 rpm.
7. Sample the flask 10 minutes after inoculation and every hour thereafter and measure the optical density of the liquid at 600 nm ($OD_{600}$). Obtain an approximately 1.0 mL sample and dilute accordingly with USP water. Record the results on the data sheet. (Note: for bacterial cell cultures, $OD_{600}$ of $1.0=8\times10^8$ cells/mL).
8. Graph the growth curves—end determine the time required to reach 3 ODs.
9. Repeat steps 4-8 until ready to inoculate the 2.8 L shake flask.
10. Determine the $OD_{600}$ at the time of the expansion to 1000 mL in a 2.8 L shake flask.
11. Inoculate two 2.8 L shake flasks containing 990 mL of LB with 10 mL of the exponentially growing culture.
12. Incubate for the predetermined amount of time at 37° C. with constant shaking at 250 rpm.
  a. Label the Flasks "A" and "B" respectively and every hour thereafter measure the $OD_{600}$ until the cell density stabilizes and/or begins to decline. Record results on the data sheet.
  b. Flask B will be used to inoculate the XDR200
13. Determine the $OD_{600}$ of Flask B at the time of the expansion to 65 L.
14. Inoculate a 65 L culture of LB+glucose+$MgSO_4$+antifoam 204 in the XDR-200 with 1000 mL of the exponentially growing culture.
15. Sample the XDR200 10 minutes after inoculation and every 1 hour thereafter and measure the $OD_{600}$. Record the results on the data sheet.

Figure 8:
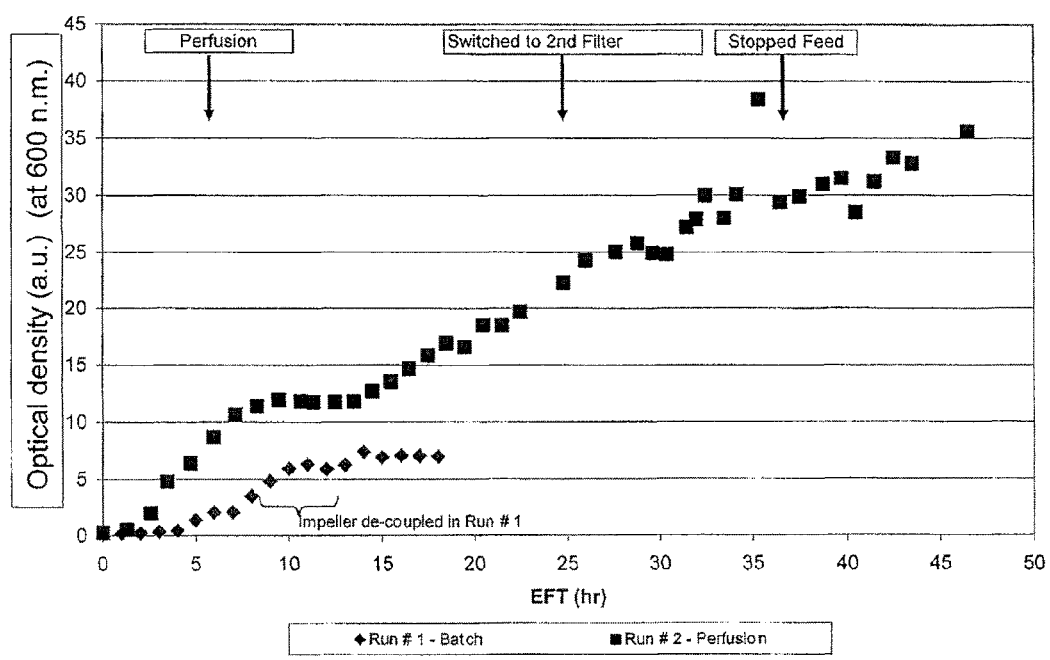
FIG. 8 is a graph showing increase in optical density of *E. Coli* cells in a bioreactor as a function of time during a continuous perfusion process.
Figure 9:
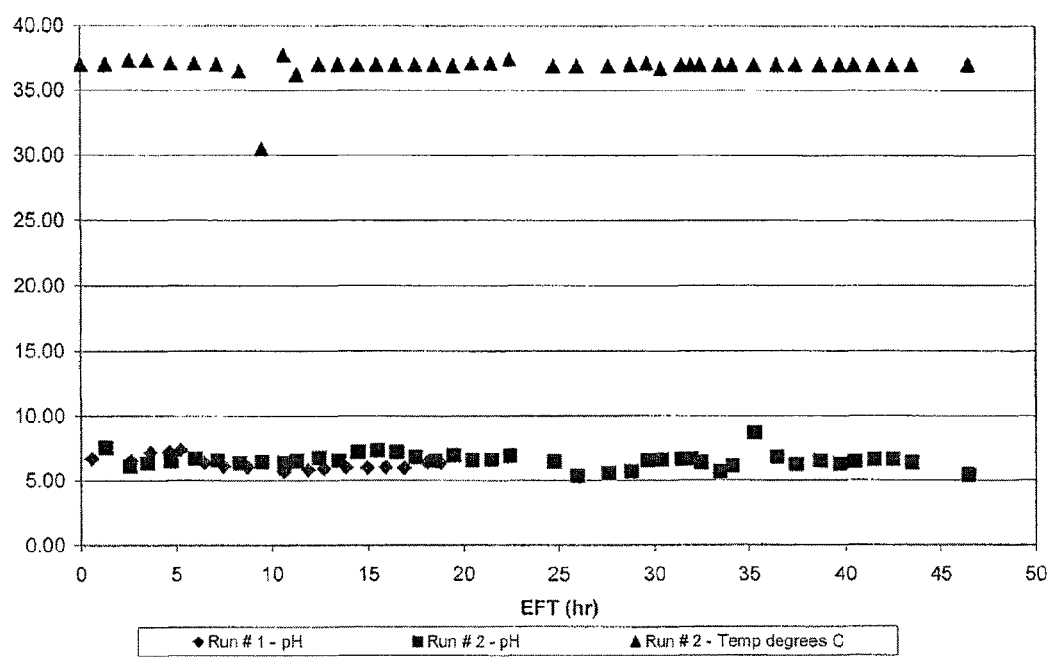
FIGS. 9-11 show measurements of various parameters in a bioreactor during performance of the process described in FIG. 8.
Figure 10:
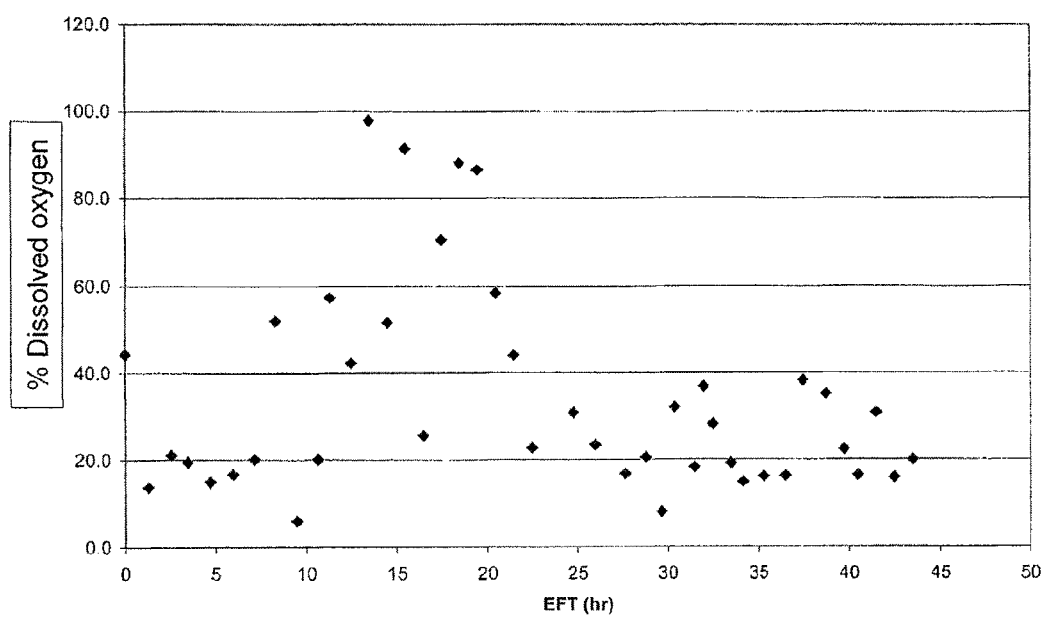
Figure 11:
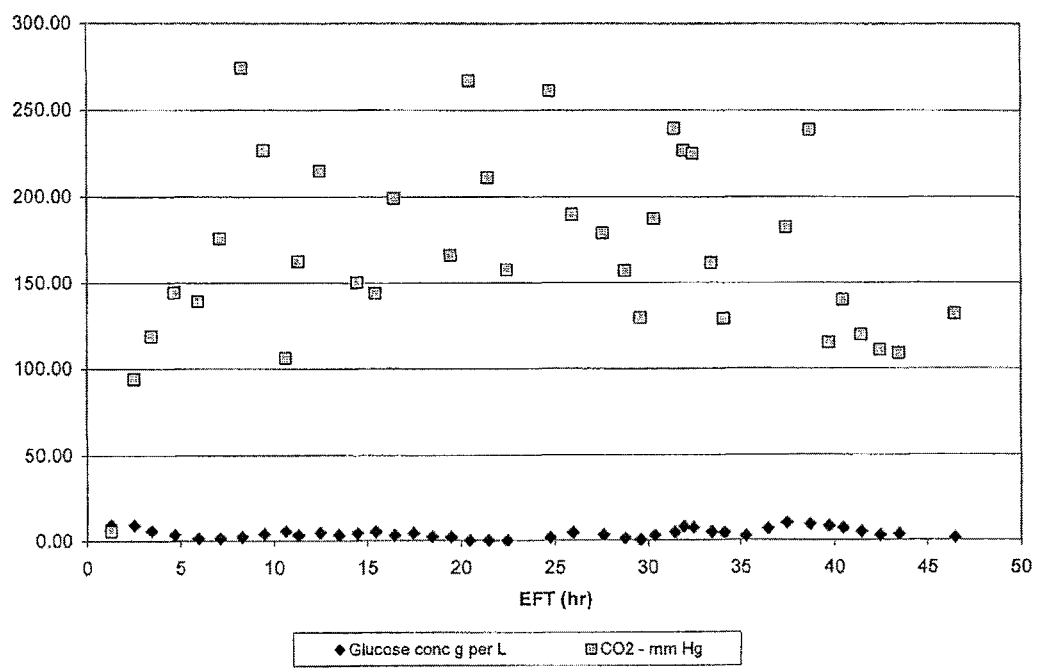

Results of the reaction are shown in FIGS. 7-10 as "Run #2". As shown in FIG. 8, cells grew during the perfusion process to an optical density of 36. FIGS. 9-11 show measurements of various parameters as a function of time.

This example shows that the bioreactor and hollow fiber cartridge combination can be operated under continuous perfusion for the recovery of E. Coli cells and maintenance of culture.

TABLE 1

XDR200 Bioreactor Parameters and Details:
XDR200 - 65L operating volume of LB with supplements 200E of LB Medium for E. Coli Perfusion Project
Supplement with 10 g/L g of glucose (2000 g)
Supplement with 0.5 g/L $MgSO_4$ (100 g)
Supplement with Antifoam at 0.02% (40 mL)
pH probe calibration: 4.01 and 7.00 standards
pH set-point of 6.8 ± 0.2
pH control - low side control - 10% NaOH
Temperature set-point of 37 ± 0.5° C.
Agitation initially at 250 rpm, increase up to 350 rpm Upward pumping
DO set-point of 20%
Overlay (Air) - 2 L/min
DO control by $O_2$ cascade and open pipe
Sparge ($O_2$) - as needed for DO control - 20 L/min max
Open pipe (Max) - 10 L/min
Open pipe Start with: (air) - 2 L/min Air
Supplement with fresh medium based upon culture glucose concentration and permeate flow rate While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

It should also be understood that, unless clearly indicated to the contrary, in any methods claimed herein that include more than one step or act, the order of the steps or acts of the method is not necessarily limited to the order in which the steps or acts of the method are recited.

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified. Thus, as a non-limiting example, a reference to "A and/or B" can refer, in one embodiment, to A only (optionally including elements other than B); in another embodiment, to B only (optionally including elements other than A); in yet another embodiment, to both A and B (optionally including other elements); etc. As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

What is claimed is:

1. A continuous perfusion bioreactor system, comprising:
   a first apparatus, comprising:
      a first disposable, flexible or collapsible bag adapted for containing a liquid and configured for use as a disposable continuous perfusion bioreactor, the first disposable, flexible or collapsible bag including a first inlet, a first outlet, and a base plate that is attached to the first disposable, flexible or collapsible bag;
      an impeller associated with the base plate;
      a first reusable support structure adapted for surrounding and supporting the first collapsible bag; and
      a second apparatus comprising a liquid-solids separation device and a second disposable, flexible or collapsible bag adapted for containing a liquid, the liquid-solids separation device in fluid communication with the first disposable, flexible or collapsible bag, and first apparatus, the liquid-solids separation device including a liquid-solids separation device inlet, and a liquid-solids separation device outlet, wherein the second apparatus is disposed external to the first disposable collapsible bag,
      and the first outlet of the first disposable collapsible bag is connected to in fluid communication with the liquid-solids separation device inlet and the liquid-solids separation device outlet is in connected to the first inlet of the first disposable collapsible bag; and
   wherein the liquid-solids separation device is configured to receive a first liquid comprising a first concentration of a component from the first disposable collapsible bag apparatus and to deliver a second liquid comprising a second concentration of the component to the first disposable collapsible bag apparatus, wherein the first and second concentrations are the same or different.

2. The system of claim 1, wherein the first and second concentrations are different.

3. The system of claim 1, wherein the second apparatus is configured to separate a component of the first liquid received from the first apparatus, the component comprising a substance chosen from a viable or non-viable organism, a precipitate, a cell, a polymeric porous or nonporous sphere, a solid sphere, a gelatinous particle, a microbead, a microdisk, a cross-linked bead, a biochemical molecular entity, and combinations thereof.

4. The system of claim 1, wherein the second apparatus is configured to separate a component of the first liquid received from the first apparatus, the component comprising a cell growing on a solid object chosen from a solid sphere, a fiber, a gelatinous particle, a polymeric particle, a non-porous particle, a porous particle, and combinations thereof.

5. The system of claim 1, wherein the second apparatus further comprises a second reusable support structure adapted for surrounding and supporting the second disposable collapsible bag.

6. The system of claim 1, wherein the fluid communication of the second apparatus with the first apparatus during use is continuous or periodic.

7. The system of claim 1, comprising at least one disposable element chosen from a disposable filtration element, a sensor, a sampling devices, a pump, a valve, and a mixer.

8. The system of claim 1, wherein the impeller is a magnetically-driven impeller.

9. The system of claim 1, wherein the impeller comprises an impeller support affixed to a side of the first disposable collapsible bag at a lower portion thereof, such that the impeller is off-center from the center of the bottom of the first disposable collapsible bag.

10. The continuous perfusion bioreactor system of claim 1, wherein the first apparatus forms at least part of a pharmaceutical manufacturing system.

11. The system of claim 1, wherein the first disposable collapsible bag has a volume of between about 1 L and about 1,000 L.

12. The system of claim 1, wherein the liquid-solids separation device is chosen from a centrifuge, a settling device, a hollow fiber filter, a flat membrane filter, a spiral wound filter, a spin filter, depth filters, tangential flow filters, microporous flow filters, ultrafiltration filters, a plate and frame filtration device, and combinations thereof.

13. The system of claim 1, wherein the liquid-solids separation device is positioned on a surface of the first disposable collapsible bag.

14. The system of claim 13, wherein the liquid-solids separation device comprises a device chosen from a microporous frit, an ultrafiltration membrane, a spin filter, a centrifuge, and a settling device.

15. The system of claim 1, wherein at least one of the first apparatus and the second apparatus is associated with its own ventilation system, cooling system, feedback control system, component that can allow one or both of the apparatuses to be operated independently of one another, and combinations thereof.

16. The system of claim 1, wherein the first disposable collapsible bag comprises one or more internal partitions.

17. The system of claim 1,
wherein at least one of the first apparatus and the second apparatus is in the form of a portable module, and
wherein upon fluid communication between the first and second apparatuses, each apparatus can be moved relative to the other without breaking the connection therebetween.

18. A method of using the continuous perfusion bioreactor system of claim 1 to perform a separation, comprising:
transferring a first liquid comprising a plurality of substances chosen from biochemical solutes, particulates, solid objects, and combinations thereof from the first disposable collapsible bag to the liquid-solids separation device;
separating at least a portion of the plurality of the biochemical solutes, particulates, solid objects, or a combination thereof from the first liquid in the liquid-solids separation device; and
transferring a second liquid from the liquid-solids separation device to the first collapsible bag, wherein the first and second liquids have different concentrations of the biochemical solutes, particulates, solid objects, or a combination thereof, thereby performing the separation.

19. The method of claim 18, wherein at least a portion of the plurality of biochemical solutes, particulates, solid objects, or a combination thereof separated from the first liquid in the liquid-solids separation device second apparatus are chosen from biochemicals, cells, solids with or without cells on the surface, semi-rigid spheres, polymeric spheres, precipitates, and combinations thereof, and
the second liquid transferred from the liquid-solids separation device second apparatus to the first collapsible bag comprises a greater concentration of the biochemical solutes, particulates, solid objects, or a combination thereof than the concentration of biochemical solutes, particulates, solid objects, or a combination thereof in the first liquid, thereby flowing some or all of the separated biochemical solutes, particulates, solid objects, or a combination thereof back into the first collapsible bag.

20. A method of recovering and recycling solutes or cells from a continuous perfusion bioreactor comprising the first collapsible bag of the system of claim 1, while maintaining a substantially constant volume of liquid in the continuous perfusion bioreactor, the method comprising:
allowing a cell culture suspension in a liquid medium in the first collapsible bag to grow to a first concentration of solutes or cells;
continuously allowing a portion of the liquid medium comprising the solute or cell culture suspension having the first concentration of solutes or cells to flow out of the first outlet of the first collapsible bag and into the second liquid-solids separation device inlet;
allowing the liquid-solids separation device to separate out at least a portion of the solutes or cells from the liquid medium flowing into the liquid-solids separation device from the first collapsible bag, while simultaneously causing a liquid to flow from the liquid-solids separation device out of the second liquid-solids separation device outlet and into the first inlet of the first collapsible bag; and
recycling at least a portion of the solutes or cells separated out by the liquid-solids separation device by flowing some or all of the separated solutes or cells back into the first collapsible bag, while continuously maintaining a substantially constant volume within the first collapsible bag during the outflowing, inflowing, and recycling steps, thereby recovering and recycling solutes or cells from the disposable continuous perfusion bioreactor while maintaining a substantially constant volume of liquid in the disposable continuous perfusion bioreactor.

* * * * *